(12) United States Patent  
Yacoby-Zeevi et al.

(10) Patent No.: US 9,415,108 B2
(45) Date of Patent: Aug. 16, 2016

(54) COMPOSITIONS FOR TRANSDERMAL DELIVERY OF ACTIVE AGENTS

(75) Inventors: Oron Yacoby-Zeevi, Moshav Bitsaron (IL); Mara Nemas, Gedera (IL); Eduardo Zawoznik, Mazkeret Batya (IL)

(73) Assignee: NeuroDerm, Ltd., Rehovot (IL)

( * ) Notice: Subject to any disclaimer, the term of this patent is extended or adjusted under 35 U.S.C. 154(b) by 401 days.

(21) Appl. No.: 13/885,512

(22) PCT Filed: Nov. 15, 2011

(86) PCT No.: PCT/IL2011/000880
§ 371 (c)(1),
(2), (4) Date: Aug. 29, 2013

(87) PCT Pub. No.: WO2012/066537
PCT Pub. Date: May 24, 2012

(65) Prior Publication Data
US 2013/0338143 A1 Dec. 19, 2013

Related U.S. Application Data

(60) Provisional application No. 61/413,608, filed on Nov. 15, 2010.

(51) Int. Cl.
*A61K 31/00* (2006.01)
*A61K 47/10* (2006.01)
(Continued)

(52) U.S. Cl.
CPC .............. *A61K 47/10* (2013.01); *A61K 9/0014* (2013.01); *A61K 31/137* (2013.01);
(Continued)

(58) Field of Classification Search
CPC ....... A61K 47/10; A61K 47/06; A61K 47/14; A61K 47/12; A61K 47/183; A61K 31/138; A61K 31/4166; A61K 31/137; A61K 31/49; A61K 31/167; A61K 31/407; A61K 31/4402; A61K 31/55; A61K 31/554; A61K 31/277; A61K 31/198; A61K 31/5377; A61K 31/465; A61K 9/0014; A61K 31/00138
USPC ............................................. 514/211, 211.07
See application file for complete search history.

(56) References Cited

U.S. PATENT DOCUMENTS

2007/0269379 A1* 11/2007 Mitragotri et al. ............. 424/9.2
2012/0004305 A1 1/2012 Miura et al.
(Continued)

FOREIGN PATENT DOCUMENTS

EP 0189861 A2 8/1986
EP 2407179 A1 1/2012
(Continued)

OTHER PUBLICATIONS

Williams et al. (2004) "Penetration Enhancers," *Advanced Drug Delivery Reviews* 56(5):603-618.
(Continued)

*Primary Examiner* — T. Victor Oh
(74) *Attorney, Agent, or Firm* — Goodwin Procter LLP

(57) ABSTRACT

Disclosed herein are compositions that are useful in effecting the transdermal delivery of therapeutic agents. More particularly, the disclosed transdermal compositions may include a fatty alcohol (for example, octanol), a terpene (for example, limonene), and an active agent comprising an amine moiety.

18 Claims, 34 Drawing Sheets

(51) Int. Cl.
*A61K 9/00* (2006.01)
*A61K 31/167* (2006.01)
*A61K 31/198* (2006.01)
*A61K 31/277* (2006.01)
*A61K 31/407* (2006.01)
*A61K 31/4402* (2006.01)
*A61K 31/465* (2006.01)
*A61K 31/49* (2006.01)
*A61K 31/5377* (2006.01)
*A61K 31/55* (2006.01)
*A61K 31/554* (2006.01)
*A61K 47/06* (2006.01)
*A61K 47/12* (2006.01)
*A61K 47/14* (2006.01)
*A61K 47/18* (2006.01)
*A61K 31/137* (2006.01)
*A61K 31/138* (2006.01)
*A61K 31/4166* (2006.01)

(52) U.S. Cl.
CPC ............ *A61K 31/138* (2013.01); *A61K 31/167* (2013.01); *A61K 31/198* (2013.01); *A61K 31/277* (2013.01); *A61K 31/407* (2013.01); *A61K 31/4166* (2013.01); *A61K 31/4402* (2013.01); *A61K 31/465* (2013.01); *A61K 31/49* (2013.01); *A61K 31/5377* (2013.01); *A61K 31/55* (2013.01); *A61K 31/554* (2013.01); *A61K 47/06* (2013.01); *A61K 47/12* (2013.01); *A61K 47/14* (2013.01); *A61K 47/183* (2013.01)

(56) References Cited

U.S. PATENT DOCUMENTS

| | | |
|---|---|---|
| 2012/0004306 A1 | 1/2012 | Miura et al. |
| 2014/0051755 A1 | 2/2014 | Yacoby-Zeevi et al. |

FOREIGN PATENT DOCUMENTS

| | | |
|---|---|---|
| JP | 2000/038338 A | 2/2000 |
| WO | WO-00/47208 A1 | 8/2000 |
| WO | WO-03/086331 A1 | 10/2003 |
| WO | WO-2010/103843 A1 | 9/2010 |
| WO | Wo-2010/103844 A1 | 9/2010 |
| WO | WO-2010/103845 A1 | 9/2010 |
| WO | WO-2012/066537 A2 | 5/2012 |
| WO | WO-2014/141261 A1 | 9/2014 |

OTHER PUBLICATIONS

International Search Report for PCT/IL2011/000880 mailed Jun. 4, 2012 (6 pages).
Written Opinion of the International Searching Authority for PCT/IL2011/000880 mailed Jun. 4, 2012 (10 pages).
Pappert, et al., (1997) "Clinical/Scientific Notes—The Stability of Carbidopa in Solution," Movement Disorders, vol. 12, pp. 608-610.
International Search Report for PCT/IL2015/050258, mailed Aug. 13, 2015 (3 pages).
Written Opinion for International Application No. PCT/IL2015/050258, mailed Aug. 13, 2015 (6 pages).

* cited by examiner

| Formulation # | 1 | 2 | 3 | 4 | 5 | 6 | 7 | 8 |
|---|---|---|---|---|---|---|---|---|
| Octanol | 0 | 2.5 | 0 | 4 | 4 | 2.5 | 2.5 | 0 |
| Limonene | 1.5 | 0 | 1 | 0 | 1 | 1 | 0 | 1 |
| Lauroglycol | 0 | 2.5 | 2.5 | 2 | 2 | 1.5 | 1.5 | 1.5 |
| 24h | 1.0 | 3.6 | 2.2 | 6.6 | 11.1 | 5.3 | 2.4 | 1.9 |
| 41h | 1.2 | 5.4 | 3.3 | 17.5 | 21.8 | 13.4 | 9.4 | 2.7 |

|  | Formulation # 3 Limonene+LG | Formulation #4 Octanol + LG | Formulation #5 Lim+Oct +LG | Formulation #3+4 (calculated) (Lim+LG) + (Octanol+LG) |
|---|---|---|---|---|
| 41h | 3.3 | 17.5 | 21.8 | 20.8 |
| 24h | 2.2 | 6.6 | 11.1 | 8.8 |

|  | Formulation # 8 Limonene+LG | Formulation #7 Octanol + LG | Formulation #6 Lim+Oct +LG | Formulation #7+8 (calculated) (Lim+LG) + (Octanol+LG) |
|---|---|---|---|---|
| 41h | 2.7 | 9.4 | 13.4 | 12.1 |
| 24h | 1.9 | 2.4 | 5.3 | 4.3 |

| Composition | TD-CD-Arg-10 | TD-CD-Arg-15 |
|---|---|---|
| PG:PEG 300 (50:50) (%) | 75.75 | 74.25 |
| H2O (%) | 4 | 4 |
| Sodium metabisulfate (%) | 0.2 | 0.2 |
| CD-Arg (%) | 14.5 | 14.5 |
| Ascorbyl palmitate (%) | 0.05 | 0.05 |
| 1-Octanol (%) | 4 | 4 |
| Lactic acid (%) | 0 | 1.5 |
| Limonene (%) | 1.5 | 1.5 |
| pH | 9.08 | 6.85 |

| Composition | TD-CD-Arg-17 | TD-CD-Arg-17 (Gel) |
|---|---|---|
| PG (%) | 61 | 56 |
| PEG 300 (%) | 15.3 | 14.0 |
| H2O (%) | 4.0 | 3.7 |
| Sodium metabisulfite (%) | 0.2 | 0.2 |
| CD-Arg (%) | 14.5 | 13.3 |
| Ascorbyl palmitate (%) | 0.05 | 0.05 |
| 1-Octanol (%) | 2.0 | 1.85 |
| Lactic acid (%) | 1.5 | 1.4 |
| Limonene (%) | 1.5 | 1.4 |
| Klucel (HPMC) (%) | 0 | 8 |

| Composition | TD-CD-49 | TD-LD-1 |
|---|---|---|
| PG (%) | 67.8 | 54.9 |
| H$_2$O (%) | 5.2 | 5.2 |
| Sodium metabisulfite (%) | 0.2 | 0.2 |
| CD (%) | 6.8 | 0.0 |
| L-dopa (%) | 0.0 | 7.1 |
| Arginine (%) | 7.5 | 13.1 |
| Lactic acid (%) | 1.2 | 8.5 |
| Ascorbyl palmitate (%) | 0.07 | 0.07 |
| 1-Octanol (%) | 4.0 | 4.0 |
| Limonene (%) | 1.2 | 1.1 |
| Lauroglycol 90 (%) | 2.0 | 2 |
| Klucel (%) | 4.2 | 4.1 |
| pH | 6.1 | 5.3 |

Effect of Organic Acids on the
Transdermal Delivery of Opipramol, t=46h

| Composition | % | pH |
|---|---|---|
| Opipramol base | 5 | |
| Succinic acid | 2eq | |
| Citric acid | 1eq | |
| Lactic acid | 1eq | |
| Ascorbic acid | 1eq | 6 |
| Malic acid | 1eq | 4.5 |
| Tartaric acid | 1eq | 5 |
| Octanol | 4 | |
| Lauroglycol | 2 | |
| klucel | 2 | |
| Propylene Glycol | Complete to 100% | |

Transdermal Delivery of Opipramol (mg/cm²)

| Formulation # | 1 | 2 | 3 | 4 | 5 | 6 |
|---|---|---|---|---|---|---|
| Octanol | 4 | 4 | 4 | 0 | 4 | 0 |
| Lauroglycol | 2 | 2 | 0 | 2 | 0 | 2 |
| Limonene | 0 | 1 | 0 | 0 | 1 | 1 |
| 24h | 0.6 | 3.1 | 0.3 | 0.2 | 5.5 | 0.3 |
| 42h | 1.7 | 5.9 | 0.9 | 0.3 | 9.7 | 0.7 |

The Synergistic Effect between Octanol (O) and Limonene (L) or Lauroglycol (LG) and the Inhibitory Effect between Lauroglycol and Limonene

| | Experimental | | | | | | Calculated | |
|---|---|---|---|---|---|---|---|---|
| | O F #3 | LG F #4 | LG/O F #1 | LG/L F #6 | L/O F #5 | L/LG/O F #2 | LG+L+O F#1+6 | LG+O F#4+3 |
| 24h | 0.3 | 0.2 | 0.6 | 0.3 | 5.5 | 3.1 | 0.9 | 0.5 |
| 42h | 0.9 | 0.3 | 1.7 | 0.7 | 9.7 | 5.9 | 2.4 | 1.2 |

Effect of Glutamic Acid on the Transdermal Delivery of Opipramol Through Full Thickness Porcine Skin Ex-Vivo

| Composition # | 1 | 2 | 3 | 4 | 5 |
|---|---|---|---|---|---|
| Opipramol base (%) | 5 | 5 | 5 | 5 | 5 |
| Glutamic acid (%) | 0 | 0 | 2 | 2 | 2 |
| Octanol (%) | 4 | 4 | 4 | 4 | 4 |
| Lauroglycol 90 (%) | 2 | 2 | 2 | 2 | 2 |
| Limonene (%) | 0 | 1 | 0 | 1 | 0 |
| Klucel (%) | 2 | 2 | 2 | 2 | 2 |
| Water (%) | 0 | 5 | 0 | 5 | 5 |
| PG (%) | 87 | 81 | 85 | 79 | 80 |

| Formulation # | 1 | 2 | 3 | 4 | 5 |
|---|---|---|---|---|---|
|  | LG/O | LG/O/L/W | LG/O | LG/O/L/W | LG/O/W |
| Glutamic Acid | No |  | Yes |  |  |
| 23h | 0.6 | 0.8 | 1.2 | 3.7 | 5.4 |
| 40h | 1.1 | 1.4 | 4.4 | 7.1 | 11.0 |

| | 1 | 2 | 3 | 4 |
|---|---|---|---|---|
| Ditiazem base (%) | 5 | 5 | 5 | |
| Diltiazem HCl (%) | | | | 5.4 |
| Tartaric acid (%) | 1.8 | 1.8 | | |
| Octanol (%) | 4 | 4 | 4 | 4 |
| Lauroglycol 90 (%) | 2 | 2 | 2 | 2 |
| Limonene (%) | | 1 | 1 | 1 |
| Water (%) | | 5 | 5 | 5 |
| Klucel (%) | 2 | 2 | 2 | 2 |
| PG (%) | 85.2 | 79.2 | 81.0 | 80.6 |
| Ph | | | | 2.9 |

The Effect of LG and Tartaric Acid on the Transdermal Delivery of Quetiapine Through Full Thickness Porcine Skin Ex Vivo

| Composition | 1 | 2 | 3 | 4 |
|---|---|---|---|---|
| Quetiapine fumarate | 5.75 | 5.75 | 5.75 | |
| Quetiapine base | | | | 5 |
| Tartaric acid | | 1 | 1 | |
| Octanol | 4 | 4 | 4 | 4 |
| Lauroglycol | 2 | 2 | 0 | 2 |
| Limonene | 1 | 1 | 1 | 1 |
| Water | 5 | 5 | 5 | 5 |
| Klucel | 2 | 2 | 2 | 2 |
| PG | 80.25 | 79.25 | 81.25 | 81.00 |

|  | 1 | 2 | 3 |
|---|---|---|---|
| Phenytoin | 5 | 5 | 5 |
| L-arginine | 5.2 | 5.2 |  |
| NaOH |  |  | 0.8 |
| Octanol | 4 | 4 | 4 |
| Lauroglycol | 2 | 2 | 2 |
| Limonene |  | 1 | 1 |
| Water |  | 5 | 0.9 |
| Klucel | 2 | 2 | 2 |
| PG | 81.8 | 75.8 | 85.1 |

| | 1 | 2 | 3 |
|---|---|---|---|
| PG | 78.05 | 80.05 | 79.05 |
| Entacapone | 5 | 5 | 5 |
| L-Arginine | 2.85 | 2.85 | 2.85 |
| Na Bisulfite | 0.1 | 0.1 | 0.1 |
| Octanol | 4 | 4 | 4 |
| Lauroglycol 90 | 2 | 0 | 2 |
| Limonene | 1 | 1 | 0 |
| Water | 5 | 5 | 5 |
| Klucel | 2 | 2 | 2 |

| Formulation | 1 | 2 | 3 |
|---|---|---|---|
| Octanol | + | + | + |
| Limonene | + | + | - |
| Lauroglycol | + | - | + |
| Rate ($\mu g/h/cm^2$) | 90 | 135 | 42 |

| Ingredient | TF-2 (TD-CD-arg-48) | TF-4 (TD-CD-arg-74) |
|---|---|---|
| PG (%) | 59.34 | 64.34 |
| H2O (%) | 5.00 | 10.00 |
| Sodium metabisulfite (%) | 0.20 | 0.20 |
| EDTA (%) | 0.01 | 0.01 |
| CD-Arg (MN 26-49) (%) | 14.50 | 14.50 |
| Lactic acid (%) | 1.00 | 1.00 |
| Ascorbyl palmitate (%) | 0.05 | 0.05 |
| 1-Octanol (%) | 4.0 | 4.0 |
| Lauroglycol 90 (%) | 2.0 | 2.0 |
| Klucel (%) | 4.0 | 4.0 |

COMPOSITIONS FOR TRANSDERMAL DELIVERY OF ACTIVE AGENTS

CROSS-REFERENCE TO RELATED APPLICATIONS

This application is a national stage filing under 35 U.S.C. §371 of PCT/IL2011/000880, filed Nov. 15, 2011, which claims priority to U.S. Provisional Patent Application No. 61/413,608, filed Nov. 15, 2010, both of which are hereby incorporated by reference in their entirety.

TECHNICAL FIELD

The present invention provides compositions that are useful in effecting the transdermal delivery of therapeutic agents. More particularly, these transdermal compositions may include a fatty alcohol, e.g., octanol, a terpene, e.g., limonene, and an active agent comprising an amine moiety.

BACKGROUND ART

Active agents (for example, therapeutic agents such as drugs or immunologically active agents such as vaccines) are conventionally administered either orally or by injection. However, many active agents are completely ineffective or have radically reduced efficacy when orally administered since they either are not absorbed or are adversely affected before entering the bloodstream and thus do not possess the desired activity. On the other hand, the direct injection of active agents intravenously or subcutaneously, while assuring no modification of the agents during administration, can be invasive, painful, and often results in poor patient compliance.

Transdermal delivery of active agents, however, result in systemic circulation of the active agent and can provide an alternative mode of administration. For example, transdermal delivery can potentially provide better drug bioavailability than oral administration, in part because such delivery bypasses not only the initial metabolism of the drug by the liver and the intestines but also the unpredictable absorption of the drug from the gastrointestinal tract. Transdermal delivery also can result in more stable blood serum level of the drug (e.g., leading to a prolonged pharmacological effect that is similar to intravenous infusion), and can allow for easily adjustable dosing rate. For example, transdermal patches can be easily removed which results in rapid cessation of dosing and elimination of the drug from circulation. Finally, transdermal delivery typically results in greater patient compliance because it is non-invasive and can be easily administered.

The skin serves as a barrier to the penetration of many foreign substances. The feasibility of using transdermal delivery of active agents as a route of administration requires that a therapeutic rate of drug delivery through the skin be achieved. This can be accomplished if the skin can be made more permeable to the drug. Factors which determine the permeability of the skin to a particular drug can include drug diffusivity through the skin membrane and/or drug concentration in the vehicle. In addition, certain materials used as adjuvants in vehicles may affect the characteristics of the skin membrane barrier and thus alter the permeability of the skin to the drug. Permeation enhancers, for example, can maximize penetration rates and/or minimize lag times in drug penetration through the skin, and should be substantially non-toxic, non-irritant and non-sensitizing on repeated exposure.

However, it is often difficult to predict which compounds will work as permeation enhancers and which permeation enhancers will work for particular drugs. Consequently, there remains a need for transdermal formulations that could deliver, at controlled rates, an active agent or a mixture thereof, combined with appropriate permeation enhancers.

SUMMARY OF INVENTION

Provided herein are pharmaceutically acceptable transdermal compositions that include an active agent, and may include a fatty alcohol and/or a terpene. Contemplated compositions provided herein may include an active agent having at least one primary, secondary or tertiary amine moiety, a negatively charged carbonyl moiety, and/or an amide moiety. In other embodiments, a disclosed composition may include an active agent that is an amino acid or amino acid derivative, for example, may include an agent chosen from: carbidopa, levodopa, and/or pharmaceutically acceptable salts thereof. In other embodiments, a disclosed composition may include an active agent selected from the group consisting of: opipramol, physostigmine, chlorpheniramine, lidocaine, metoprolol, nicotine, diltiazem, quinidine, imipramine, quetiapine, venlafaxine, and pharmaceutically acceptable salts thereof.

Disclosed compositions may have about 1 to about 10 weight percent active agent. In other embodiments, disclosed compositions may include about 0.5 to about 7.5, or about 2 to about 5 weight percent fatty alcohol, such as octanol, e.g., 1-octanol. Disclosed compositions may further include a fatty acid ester, e.g.; lauroglycol. In some embodiments, a disclosed composition may have a weight ratio of fatty alcohol to lauroglycol of about 3:1 to about 1.5:1, and/or may have about 0.1 to about 5.0 weight percent fatty acid ester. Disclosed compositions may further comprise a cellulose ester such as hydroxypropyl methyl cellulose, and/or propylene glycol.

In other embodiments, a disclosed composition may further comprise an organic acid, such as an organic acid selected from the group consisting of ascorbic acid, tartaric acid, malic acid, succinic acid, fumaric acid, citric acid, lactic acid, glutamic acid, and aspartic acid. An organic acid may be selected from the group consisting of arginine, lysine or histidine.

For example, provided herein is a pharmaceutically acceptable transdermal composition comprising octanol, limonene, and an active agent comprising an amine moiety, such as an active agent selected from the group consisting of opipramol and pharmaceutically acceptable salts thereof. Also provided herein is a pharmaceutically acceptable transdermal composition comprising octanol, limonene, and an active agent comprising an amine moiety, e.g., carbidopa, levodopa, and pharmaceutically acceptable salts thereof. A pharmaceutically acceptable transdermal composition comprising octanol, limonene, and an active agent comprising an amide moiety, e.g. entacapone, and pharmaceutically acceptable salts thereof, is also contemplated.

Disclosed compositions may include about 0.5 to about 7.5 weight percent octanol and/or about 0.5 to about 5 weight percent limonene; and optionally may further include lauroglycol. In some embodiments, if lauroglycol is present, the ratio of octanol to lauroglycol may be about 3:1 to about 1.5:1. Contemplated pharmaceutically acceptable transdermal compositions may further include arginine.

Provided herein, in some embodiments, is a disclosed pharmaceutically acceptable transdermal composition wherein the transdermal composition comprises an active agent, optionally an organic acid, octanol, and lauroglycol and/or limonene, when transdermally administered to a patient, delivers more than twice the amount of active agent to said patient over 20 hours as compared to a formulation that does not include octanol.

Also provided herein is a pharmaceutically acceptable transdermal composition comprising an active agent, optionally an organic acid, octanol, and limonene, wherein the transdermal composition, when transdermally administered to a patient, delivers more than twice the amount of active agent to said patient over 20 hours as compared to a formulation that does not include limonene. Provided herein, in some embodiments, is transdermal composition having an active agent and an organic acid, when transdermally administered to a patient, delivers more than twice the amount of active agent a to said patient over 20 hours as compared to a formulation that does not include an organic acid.

A pharmaceutically acceptable transdermal composition contemplated herein also includes an active agent, optionally an organic acid, octanol, and lauroglycol, wherein the transdermal composition, when transdermally administered to a patient, delivers more than twice the amount of active agent to the patient over 20 hours as compared to a formulation that does not include lauroglycol.

Provided herein, in some embodiments, is a transdermal composition having an active agent, and organic acid, octanol, and laoroglycol and/or limonene. Such a composition, when transdermally administered to a patient, may deliver more than twice the amount of active agent to said patient over 20 hours as compared to a formulation that does not include an organic acid.

Also provided herein is pharmaceutically acceptable transdermal composition comprising octanol tartaric acid; and an active agent, and limonene and/or lauroglycol.

In some embodiments, provided herein is a pharmaceutically acceptable transdermal composition comprising: octanol, lauroglycol, organic acid, optionally a basic amino acid, and an active agent comprising an amine moiety or an amide moiety.

Figure 1:
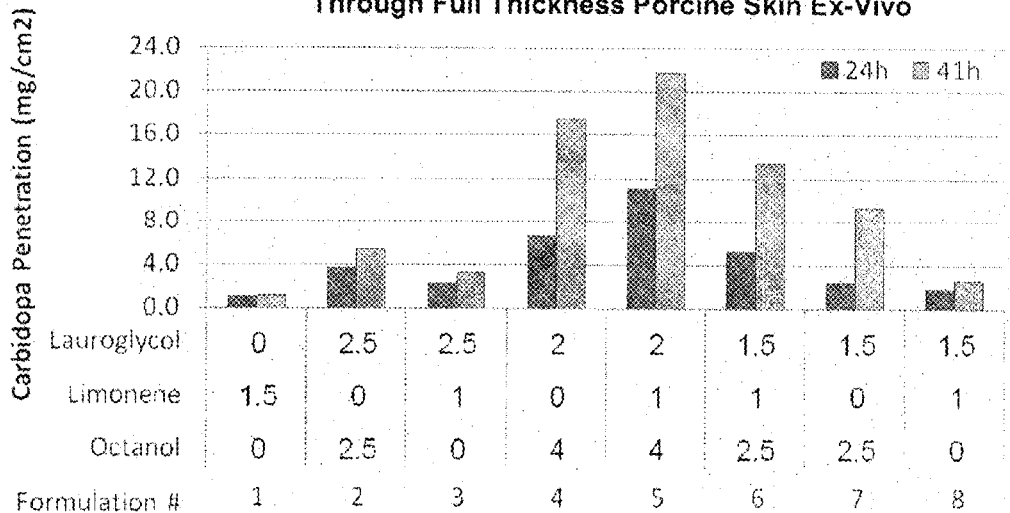
FIG. 1 depicts the effects of limonene, octanol and lauroglycol on the transdermal delivery of carbidopa/arginine salt through porcine skin ex vivo.

Unless indicated otherwise, all amounts indicated in the above figures are weight percent.

DETAILED DESCRIPTION OF THE INVENTION

Definitions

For convenience, certain terms used in the specification, examples, and appended claims are collected in this section.

The term "therapeutically effective amount" refers to the amount of an active ingredient, or combination of active ingredients, that will elicit the biological or medical response that is being sought by the researcher, veterinarian, medical doctor or other clinician. Alternatively, a therapeutically effective amount of an active ingredient is the quantity of the compound required to achieve a desired therapeutic and/or prophylactic effect, such as the amount of the active ingredient that results in the prevention of or a decrease in the symptoms associated with the condition (for example, to meet an end-point).

The terms "pharmaceutically acceptable" or "pharmacologically acceptable" refer to molecular entities and compositions that do not produce an adverse, allergic or other untoward reaction when administered to an animal, or to a human, as appropriate. The term, "pharmaceutically acceptable carrier" includes any and all solvents, dispersion media, coatings, antibacterial and antifungal agents, isotonic and absorption delaying agents and the like. The use of such media and agents with pharmaceutical active agents is well known in the art. In some embodiments, supplementary active ingredients can also be incorporated into the compositions.

The terms "carriers" or "vehicles" as used herein refer to carrier materials suitable for transdermal drug administration. Contemplated carriers and/or vehicles include any such materials known in the art, which are substantially nontoxic and/or do not interact with other components of a pharmaceutical formulation or drug delivery system in a deleterious manner. Examples of specific suitable carriers and vehicles for use herein include water, propylene glycol, mineral oil, silicone, inorganic gels, aqueous emulsions, liquid sugars, waxes, petroleum jelly, and/or other oils and polymeric materials.

The term "transdermal" refers generally to passage of an agent across the skin layers. For example, the term "transdermal" may refer to delivery of an agent (e.g., a vaccine or a drug) through the skin to the local tissue or systemic circulatory system without substantial cutting or penetration of the skin, such as cutting with a surgical knife or piercing the skin with a hypodermic needle. Transdermal agent delivery includes delivery via passive diffusion.

The terms "penetration enhancement" or "permeation enhancement" as used herein refer to an increase in the permeability of skin to a pharmacologically active agent, i.e., so as to increase the rate at which the active agent permeates through the skin and enters the bloodstream. The enhanced permeation effected through the use of skin permeation enhancers, for example, through the use of a composition disclosed herein, can be observed by e.g., measuring the rate of diffusion of drug ex-vivo, i.e., through animal or human skin using a diffusion cell apparatus, or in-vivo, as described in the examples herein.

The terms, "individual," "patient," or "subject" are used interchangeably herein and include any mammal, including animals, for example, primates, for example, humans, and other animals, for example, dogs, cats, swine, cattle, sheep, and horses. The compositions disclosed herein can be administered to a mammal, such as a human, but can also be other mammals, for example, an animal in need of veterinary treatment, for example, domestic animals (for example, dogs, cats, and the like), farm animals (for example, cows, sheep, pigs, horses, and the like) and laboratory animals (for example, rats, mice, guinea pigs, and the like). The subject may be in need of treatment by delivery of a therapeutic agent, for example, transcutaneous delivery of a vaccine or transdermal delivery of a drug.

Disclosed herein are transdermal compositions that may be part of, for example, a transdermal patch, ointment, cream, gel, lotion or other transdermal solution or suspension. For example, for transdermal delivery, a transdermal patch that includes a disclosed composition is contemplated, and may include a single layer adhesive patch, a multi-layer and adhesive patch, a reservoir patch, a matrix patch, a microneedle patch or an iontophoretic patch, which typically requires applying a direct current. In some embodiments, contemplated transdermal patches may be adapted for sustained release.

Contemplated transdermal drug delivery systems can, in some embodiments, rely on passive, chemical diffusion as opposed to physical, electrical, or mechanical based approaches. For example, passive transdermal systems may have a drug reservoir containing a high concentration of drug adapted to contact the skin where the drug diffuses through the skin and into the body tissues or bloodstream of a patient, Compositions In one aspect, the present invention relates to a pharmaceutically acceptable transdermal composition comprising one or more skin permeation enhancers. For example, the transdermal composition may comprise a skin permeation enhancer such as one or more fatty alcohols, fatty acids, and/or fatty acid esters, and an active agent, and/or may comprise a terpene and an active agent. Contemplated transdermal compositions may include, for example, one or more fatty alcohols, fatty acids, and/or fatty acid esters, a terpene, and an active agent.

For example, contemplated herein, in part, are transdermal compositions with two or more skin permeation enhancers, wherein the two or more skin permeation enhancers provide an additive or even a synergistic effect on the transdermal delivery of active agents. It is contemplated that the use of two or more disclosed skin permeation enhancers, each increasing skin permeability via a different mechanism, may be additive in their enhancing effects. In an embodiment, a disclosed combination of enhancers may even have a synergistic effect on skin penetration, i.e. an effect that is greater than the sum of the individual effects of the enhancers alone.

For example, in a transdermal composition that includes octanol and limonene, the octanol and limonene may act to provide enhanced transdermal delivery of active agents e.g., may provide for a larger transdermal delivery amount of an active agent that is more than the sum transdermal delivery amount of a composition that included the active agent and limonene and transdermal delivery amount of a composition that included an active agent and octanol, e.g., a synergistic transdermal composition. In another embodiment, such a composition that includes octanol and limonene, optionally may include lauroglycol and/or an inorganic or organic acid.

In some embodiments, compositions contemplated herein may be a gel, gel-like, or liquid at room temperature.

Fatty alcohols contemplated for use in disclosed compositions, include, but are not limited to, 1-octanol, 2-octanol, 3-octanol, 4-octanol, hexanol, heptanol, nonanol, decanol (capric alcohol), undecaonl, dodecanol (lauryl alcohol), 2-ethyl hexanol, pelargonic alcohol, myristyl alcohol, cetyl alcohol, palmitoleyl alcohol, octadeconal (stearyl alcohol), isostearyl alcohol, isolauryl alcohol, isomyristyl alcohol, isopalmityl alcohol, isostearyl alcohol, elaidyl alcohol, oleyl alcohol, linoleyl alcohol, elaidolinoleyl alcohol, linoleynyl alcohol, elaidolinolenyl alcohol, ricinoleyl alcohol, arachidyl alcohol, behenyl alcohol, erucyl alcohol, lignoceryl alcohol, ceryl alcohol, montanyl alcohol, myricyl alcohol, geddyl alcohol, cetearyl alcohol, and mixtures thereof. For example, a disclosed composition may comprise about 0.1 to about 10 weight percent, for example, about 0.2 to 10 weight percent or about 0.5 to about 7.5 weight percent fatty alcohol. In an exemplary embodiment, a transdermal composition may include octanol (for example, 1-octanol).

Contemplated fatty acid esters include, but are not limited to, lauroglycol, methyl laurate, ethyl oleate, propylene glycol monolaurate, propyleneglycerol dilaurate, glycerol monolaurate, glycerol monooleate, sorbitan monooleate, isopropyl palmitate, methyl propionate, monoglycerides, sorbitan monolaurate, isopropyl n-decanoate, and oetyldodecyl myristate, and mixtures thereof. For example, a disclosed composition may comprise about 0.1 to about 10 weight percent, for example, about 0.1 to 7 weight percent or about 0.1 to about 5 weight percent (e.g., 2 weight percent) fatty acid ester, e.g., lauroglycol. In some embodiments, compositions are provided that include a fatty alcohol (e.g., octanol) and a fatty acid ester (e.g., lauroglycol) in a weight ratio of about 3:1 to about 1.5:1, or about 5:1 to about 1:1.

Contemplated fatty acids include, but are not limited to, oleic acid, alkanoic acids, capric acid, hexanoic acid, lactic acid, lauric acid, linoleic acid and mixtures thereof.

Contemplated transdermal compositions may include a terpene, i.e., a nonaromatic compound found in essential oils, which may be extracted from flowers, fruits, and other natural products. Exemplary terpenes include, but are not limited to, d-limonene, dipentene (d/l-limonene), α-pinene, γ-terpinene, β-mircene, p-cimene, α-pinene, α-phellandrene, citronellolio, geraniale (citrate), nerol, beta-carotene, menthol, geraniol, farnesol, phytol, their homologs, derivatives, enantiomers, isomers including constitutional isomers, stereoisomerisms, regioisomers, and geometric isomers, and any combinations thereof. For example, provided herein is a transdermal composition comprising 0.1 to about 10 weight percent, or about 0.2 to about 8 weight percent, or about 0.5 to about 5 weight percent terpene, e.g., d-limonene.

Contemplated transdermal compositions may further include a pharmaceutically acceptable excipient such as e.g., N-methylpyrrolidone, polyvinylpyrrolidone, propylene glycol, or polyethylene glycol, or a combination of one or more such excipients. For example, disclosed compositions may include polyols and esters thereof, such as propylene glycol, ethylene glycol, glycerol, butanediol, polyethylene glycol, polyethylene glycol monolaurate, and mixtures thereof. In some embodiments, the effect of the skin permeation enhancer in a disclosed composition may be dependent on the solvent in which they are dissolved, e.g dependent on the concentration of water and/or propylene glycol. For example, compositions that include a fatty alcohol and a terpene are provided that may further include about 0% to about 5%, or about 1% to about 10%, or about 0 to about 50%, by weight, water. Also provided herein are compositions that may include about 20 to about 98%, or about 50 to about 98%, by weight propylene glycol. Contemplated compositions may additionally include one or more antioxidants or preservatives such as, for example, N-acetyl cysteine, sodium bisulfite, sodium metabisulfite, EDTA, glutathione, and ascorbic acid.

In other embodiments, disclosed compositions may include an organic acid such as ascorbic acid, tartaric acid, malic acid, succinic acid, fumaric acid, citric acid, or lactic acid. In some embodiments, the organic acid may be an amino acid, for example, an amino acid having a pI (isoelectric point) of less than 4, such as glutamic acid or aspartic acid. In other embodiments, the organic acid may be a basic amino acid such as arginine, lysine, or histidine. Disclosed transdermal compositions, in some embodiments, may comprise about 0.1% to about 20 weight percent, for example, about 0.2 to about 15 weight percent, or about 0.5 to about 15 weight percent organic acid. In other embodiments, disclosed compositions may include an inorganic acid, e.g., hydrochloric acid.

Disclosed transdermal compositions of the present invention may further include thickening agents including cellulose ethers such as hydroxypropyl methyl cellulose, hydroxypropyl cellulose, ethylcellulose, hydroxyethyl cellulose, and carboxymethyl cellulose. For example, in one embodiment, a transdermal composition may comprise about 0.1 to about 10 weight percent, for example, about 0.1 to about 9 weight percent, or about 0.1 to about 8 weight percent of cellulose ether such as hydroxypropyl methyl cellulose and/or hydroxypropyl cellulose, for example, Klucel® hydroxypropyl cellulose.

A disclosed transdermal composition may have a physiologically acceptable pH. The term "physiologically acceptable pH" is understood to mean a pH that facilitates administration of the composition to a patient without significant adverse effects, e.g. a pH of about 4 to about 10.

Also provided herein are transdermal compositions that allow for enhanced delivery of active agents over an extended period of time. For example, a contemplated transdermal composition that includes a terpene and octanol may deliver more than two times, three times, or more of the active agent than compositions that do not include a terpene and/or octanol. In another example, a contemplated transdermal composition that includes an organic acid may deliver more than two times, three times, or more of the active agent than compositions that do not include an organic acid. In another example, a contemplated composition that includes a terpene and octanol, and an active agent, may deliver more of the active agent over a period of 1 hour, 2 hours, 5, hours, 10 hours, 20 hours, 1 day, two days, three days, or more, than compositions that include the active agent but do not include a terpene and/or octanol. In a specific embodiment, the transdermal composition when administered to a patient, may deliver more than twice of amount of carbidopa to the patient over 20 hours as compared to a transdermal formulation of carbidopa that do not include octanol. In another embodiment, a disclosed composition, when administered to a patient, may deliver more than twice of amount of opipramol, diltiazem, phenytoin, imipramine or entacapone to the patient over about 42 hours as compared to a transdermal formulation of opipramol, diltiazem, phenytoin, imipramine or entacapone that does not include limonene. For example, provided herein are compositions having opipramol or quinidine, when administered to a patient, may deliver even more than ten times of amount of e.g., opipramol or quinidine, as compared to a transdermal composition having e.g. opipramol that does not include tartaric acid. In another embodiment, compositions disclosed herein may provide more than 4 times of amount of diltiazem or quetiapine over 42 hours as compared to a trandermal formulation of one of those actives but that do not include tartaric acid.

Active Agents

Provided herein are pharmaceutically acceptable transdermal compositions that include one or more active agents. Contemplated active agents include active agents having an amine moiety (e.g. at least one primary, secondary or tertiary amine) or an active agent having a negatively charged carbonyl moiety (e.g. an amide and/or carboxyl moiety).

For example, disclosed active agents may include, but are not limited to, alkaloids (e.g., nicotine, amphetamine, lidocaine (and other caine analgesics), carbamates (e.g., pyridostigmine bromide, physostigmine), barbiturates, carbamazepines, benzodiazepines, phenothiazines, thioxanthenes, butyrophenones (e.g., haloperidol), benzamides, dibenzodiazepines, phenylindoles, benzisoxazoles (e.g., risperidone, ziprasidone), GABA-T inhibitors (e.g., vigabatrin), thienobenzaodiazepines, phenylethylamines (e.g., deprenyl HCl), SNRIs (e.g., venlafaxine HCl), SSRIs, tertiary amines (e.g., opipramol), aromatic amino acids (e.g., levodopa, carbidopa, and derivatives), DNA (e.g. supercoiled plasmid DNA), oligonucleotides (e.g., DNA, RNAi, siRNA, saRNA, µRNA), low molecular weight heparin (e.g., ardeparin), peptides (e.g., decapeptide LHRH analogues, copolymer-1, pentapeptide enkephalin), and proteins (e.g., PTH, insulin). In an embodiment, the active agent comprises an amine moiety, for example, at least one primary, secondary or tertiary amine groups. For example, the active agent may be chosen from: opipramol, diltiazem, quetiapine, quinidine, imipramine, venlafaxine, physostigmine, chlorpheniramine, metoprolol, lidocaine, apomorphine, memantine, ziprasidone, atomoxetine, sibutramine, salbutamol, phenytoin, galantamine, timolol, nicotine, methysergide, lisinopril, levosalbutamol, formotoerol, arformoterol, ipratorium bromide, voriconazole, and/or ciclopirox.

In some embodiments, the active agent may be an amino acid or amino acid derivative. For example, the active agent may be levodopa or carbidopa. In a further embodiment, the active agent comprises negatively charged carbonyl groups, e.g. amide or carboxyl groups. For example, the active agent may be entacapone, phenytoin, or carbamazepine.

Other contemplated agents include agents having a carboxylic acid group such as an agent chosen from atorvastatin, amoxicillin, fexofenadine, pravastatin, cefalexin, furosemide, ibuprofen, naproxen, gemfibrozil, mupirocin, cefprozil, methotrexate, tretinoin, cefuroxime, etodalac, penicillin, folic acid, fosinopril, ursodiol, indometacin, falsartan, lisinopril, and diclofenac (Na salt). Contemplated agents include those having primary amines (fluvoxamine, Memantine, Amlodipine, Cefdinir, Lamotrigine, Amphetamine, Triamterene, Minocycline, Phentermine, Famciclovir, Trimethoprim, Aciclovir, Hydralazine, Doxazosin, Dextroamphetamine or Famotidine); secondary amines (such as Desipramine, Atomoxetine, Azathioprine, Bromocriptine, Burpropione, Clonidine, Dexmethyl-phenidate, Duloxetine, Enalapril, Formoterol, Hydrochloro-thiazide, Lornoxicam, Metoprolol, Sertraline Paroxetine, Fluoxetine, Ramipril, Salbutamol, Bupropion, Carvedilol, Atenolol, Nifedipine, Felodipine, Enalapril, Quinapril, Tizanidine, Clonidine, Benzonatate, Propranolol HCl, Benazepril, Paroxetine, Allopurinol, Labetalol HCl, Sotalol, Torasemide, Bisoprolol, Pindolol, and Pseudo-ephedrine), tertiary amines (including for example, agents such as Miconazole, Econazole, Clotrimazole, Ketoconazole, Quinidine, Pargiline, Alprazolam, Apomorphine, Bromazepam, Burenorphine, Chlorpheniramine, Diltiazem, Dipyridamole, Domperidone, Gal antamine (HBr), Haloperidol, Hydromorphone, Levomepromazine, Methadone, Methazolamide, Metformin HCl, Azithromycin, Omeprazol, Fentanyl, Oxycodone, Risperidone, Tramadol, Citalopram, Ondansetro, Morphine, Dextropropoxyphene, Cyclobenzaprine HCl, Ciprofloxacin, Ranitidine, Verapamil, Baclofen, Oxybutynin, Venlafaxine HCl, Opipramol, Lidocaine; or amido agents such as: Oxcarbazepine, Carisoprodol, Meloxicam, Glibenclamide (glyburide), Phenytoin, Glimepiride, Barbital, Metho-carbamol, Modafinil and Entacapone.

Also contemplated are pharmaceutically acceptable salts of the disclosed active agents. Pharmaceutically acceptable salts of the disclosed therapeutic or active agents can be synthesized by conventional chemical methods. Generally, such salts can be prepared by reacting the free acid or base forms of the agents with a stoichiometric amount of the appropriate base or acid in water or in an organic solvent; or in a mixture of the two; generally, non-aqueous media like propylene glycol, ether, ethyl acetate, ethanol, isopropanol, or acetonitrile. Lists of suitable salts are found in Remington's Pharmaceutical Sciences, 20th ed., Lippincott Williams & Wilkins, Baltimore, Md., 2000, p. 704.

In some embodiments, a provided transdermal composition includes an amino acid salt of an active agent, e.g., carbidopa, levodopa, or entacapone salt with a basic amino acid selected from arginine, lysine, or histidine. In one embodiment, the salt of an active agent is the carbidopa arginine salt.

Active agents may be present in the disclosed compositions in varying amounts, e.g. a disclosed composition may include for example about 0.5 to about 10 weight percent active agent, about 1 to about 7 weight percent active agent, about 1 to 3 weight percent, about 2 to about 4 weight percent, e.g., about 2, 2.5, 3, 4, 5, or 6 weight percent. For example, contemplated herein are compositions that include about 3-8 weight percent carbidopa and/or levodopa, and about 3 to about 7 weight percent arginine, or about 3 to about 15 weight percent arginine (e.g. about 6 to about 12 weight percent carbidopa-arginine salt or levodopa-arginine salt).

In some embodiments, the disclosed transdermal composition includes biologics as active agent such as DNA, RNA, or proteins, and/or may be used for the transfection of foreign materials (e.g. supercoiled plasmid DNA, siRNA, polynucleotides, peptides, and/or proteins) into cells. For example, the disclosed transdermal composition may be used for the transfection of plasmid DNA into eukaryotic cells resulting in either transient or stable expression of the DNA. In another example, the disclosed transdermal composition may be used for the delivery peptides into eukaryotic cells. In some instances, the disclosed transdermal composition may be used for the transfection of a protein e.g. an antibody into cells.

Disclosed transdermal compositions may be used in a method of treatment for a disease in a patient in need thereof, for example a method of treatment of a disease associated with treatment by an active agent that forms part of a disclosed composition, comprising transdermally administering a disclosed composition to the patient.

EXAMPLES

The invention now being generally described, it will be more readily understood by reference to the following examples which are included merely for purposes of illustration of certain aspects and embodiments of the present invention, and are not intended to limit the invention in any way.

Example 1

Transdermal Delivery of Carbidopa Ex Vivo

The effects of octanol, limonene and/or lauroglycol on the transdermal delivery of carbidopa through full thickness pig skin are evaluated using the Franz Cell delivery system. Formulations containing carbidopa, octanol, limonene, and/or lauroglycol are prepared (formulations 1-8). Samples are collected from the receive cell at 24 and 41 hours after application of the formulation to the skin. The amount of carbidopa compounds in the receiver cell fluid is determined using a spectrophotometer and/or UV-HPLC at 280 nm.

Figure 2:
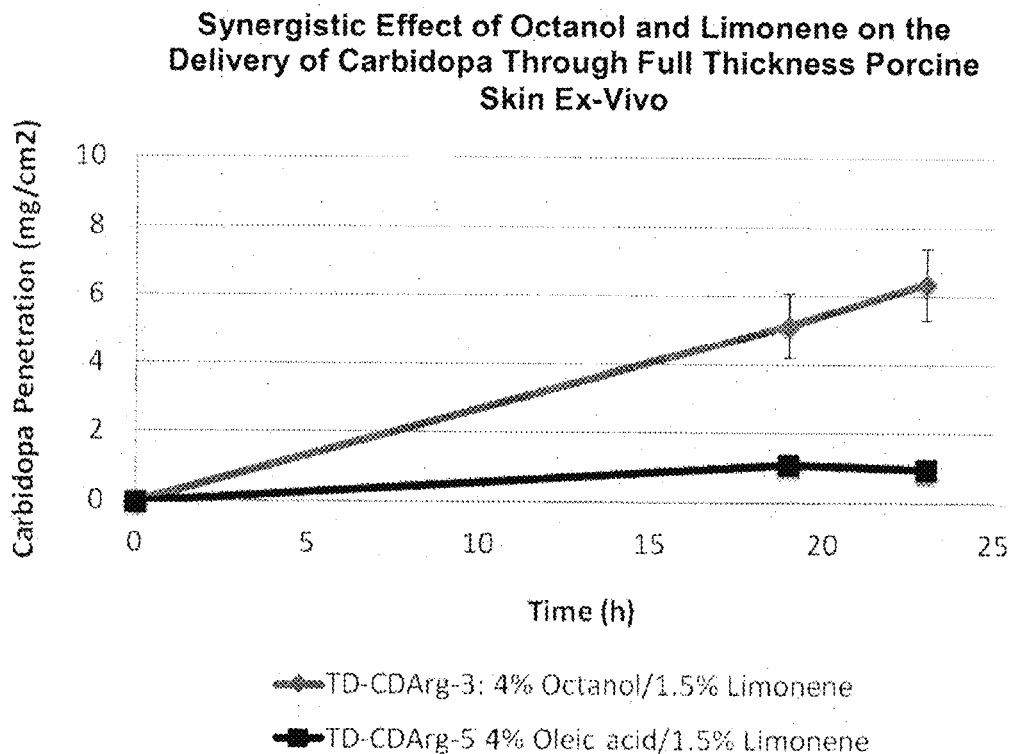
FIG. 2 depicts the effects of octanol and limonene on transdermal delivery of carbidopa/arginine salt through porcine skin ex vivo.

FIGS. 1 and 2, and Table 1 (corresponding to FIG. 1) and Table 2 (corresponding to FIG. 2) indicate that the combination of octanol and limonene provides an additive and/or synergistic effect on the delivery of carbidopa through pig skin, ex vivo. For example, as depicted in FIG. 1, application of formulation 6 which includes a combination of octanol, limonene, and lauroglycol results in greater carbidopa penetration through the skin than the combination of octanol and lauroglycol (formulation 7) or limonene (Lim) and lauroglycol (LG) (formulation 8). In Table 1 and FIG. 1, the formulations each contain 14.5% (by weight) carbidopa-arginine salt.

TABLE 1

Transdermal delivery of Carbidopa (mg/cm$^2$) through full thickness pig skin, ex vivo

| | Formulation # | | | | | | | |
|---|---|---|---|---|---|---|---|---|
| | 1 | 2 | 3 | 4 | 5 | 6 | 7 | 8 |
| Octanol | 0 | 2.5 | 0 | 4 | 4 | 2.5 | 2.5 | 0 |
| Limonene | 1.5 | 0 | 1 | 0 | 1 | 1 | 0 | 1 |
| Lauroglycol | 0 | 2.5 | 2.5 | 2 | 2 | 1.5 | 1.5 | 1.5 |
| 24 h | 1.0 | 3.6 | 2.2 | 6.6 | 11.1 | 5.3 | 2.4 | 1.9 |
| 41 h | 1.2 | 5.4 | 3.3 | 17.5 | 21.8 | 13.4 | 9.4 | 2.7 |

| | Formulation #3 Limonene + LG | Formulation #4 Octanol + LG | Formulation #5 Lim + Oct + LG | Formulation #3 + 4 (calculated) (Lim + LG) + (Octanol + LG) |
|---|---|---|---|---|
| 41 h | 3.3 | 17.5 | 21.8 | 20.8 |
| 24 h | 2.2 | 6.6 | 11.1 | 8.8 |

| | Formulation #8 Limonene + LG | Formulation #7 Octanol + LG | Formulation #6 Lim + Oct + LG | Formulation #7 + 8 (calculated) (Lim + LG) + (Octanol + LG) |
|---|---|---|---|---|
| 41 h | 2.7 | 9.4 | 13.4 | 12.1 |
| 24 h | 1.9 | 2.4 | 5.3 | 4.3 |

In Table 2 the formulations each contain 8.85% (by weight) carbidopa-arginine salt.

TABLE 2

Transdermal delivery of Carbidopa (mg/cm$^2$) through full thickness pig skin, ex vivo

| Octanol | 0 | 4 | 0 |
|---|---|---|---|
| Limonene | 1.5 | 1.5 | 1.5 |
| Oleic Acid | 0 | 0 | 2 |
| 24 h | 1.0 | 6.4 | 1.0 |

FIG. 1 also indicates that the combination of octanol and lauroglycol enhances the delivery of carbidopa through pig skin, ex vivo. This effect, however, depends on the ratio between the octanol and lauroglycol in the formulation.

Figure 3:
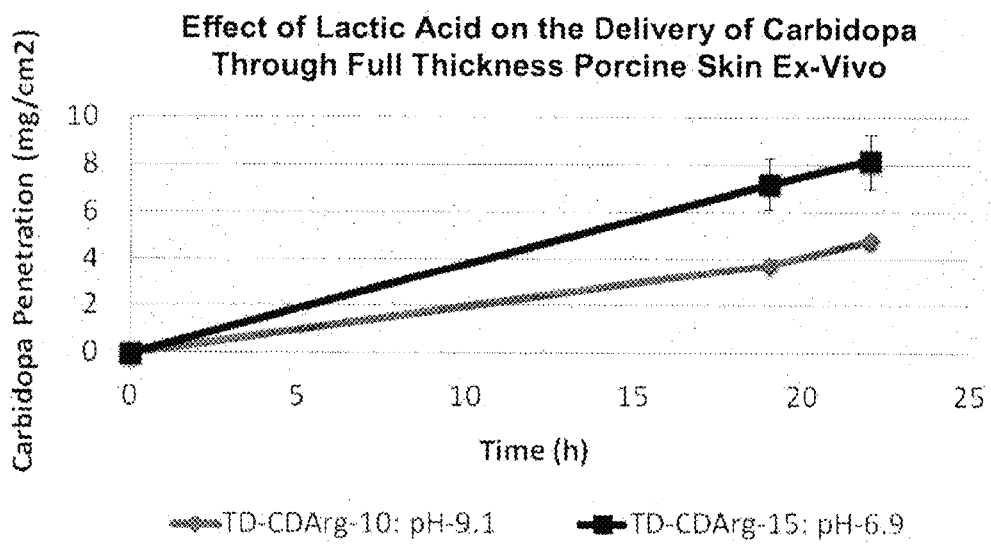
FIG. 3 depicts the effect of lactic acid and/or pH on the transdermal delivery of carbidopa/arginine salt through porcine skin ex vivo.

FIG. 3 depicts the effect of lactic acid on the transdermal delivery of carbidopa through pig skin, ex vivo. The addition of lactic acid into a carbidopa formulation containing octanol and limonene results in a reduction in pH and reduces the lag time of carbidopa penetration through the skin.

Figure 4:
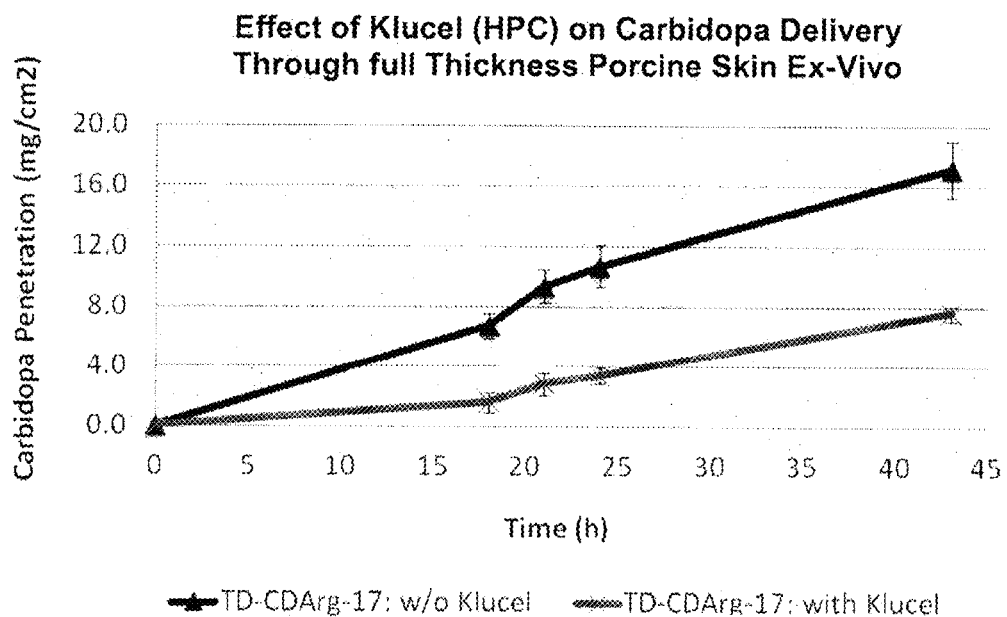
FIG. 4 depicts the effects of hydroxypropylcellulose on the transdermal delivery of carbidopa/arginine salt through porcine skin ex vivo.

FIG. 4 depicts the effect of Klucel® hydroxypropyl cellulose on the transdermal delivery of carbidopa. The inclusion of Klucel® into a carbidopa formulation containing octanol and limonene not only reduces the rate of carbidopa penetration through the skin but also increases the lag time of carbidopa penetration.

Figure 5:
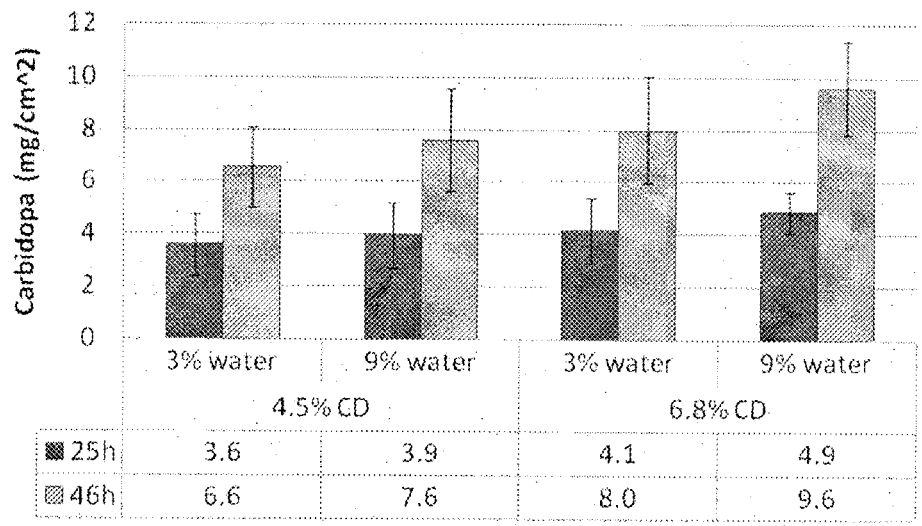
FIG. 5 depicts the effects of carbidopa and water concentration on the transdermal delivery of carbidopa through porcine skin ex vivo.

FIG. 5 depicts the effect of carbidopa concentration and water on the transdermal delivery of carbidopa. Increasing the amount of carbidopa in a formulation by 50% enhances the penetration of the drug through the skin by 25%.

Example 2

Transdermal Delivery of Carbidopa or Levodopa Ex Vivo

The transdermal delivery of levodopa through full thickness pig skin is evaluated using the Franz Cell delivery system. Formulations containing carbidopa or levodopa, octanol, limonene, and lauroglycol are prepared. Samples are collected from the receiver cells at 24 hours at 18 and 222 hours after application of the formulation to the skin. The amount of carbidopa or levodopa compounds in the receiver cell fluid is determined using a spectrophotometer and/or UV-HPLC at 280 nm.

Figure 6:
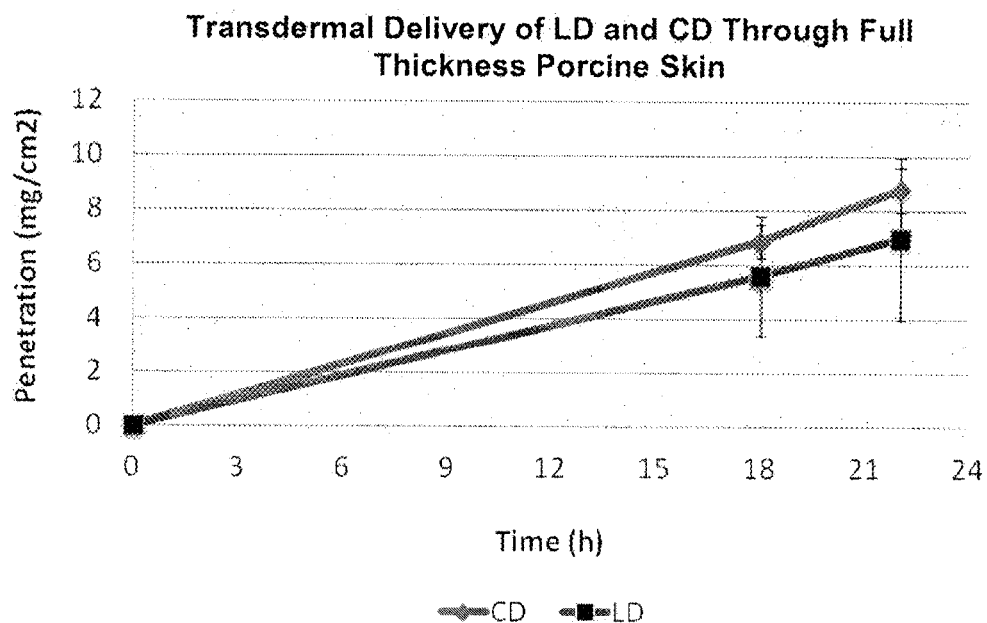
FIG. 6 depicts the transdermal delivery of carbidopa/arginine and levodopa/arginine through porcine skin ex vivo.

As depicted in FIG. 6, a gel formulation containing a carbidopa+arginine or levodopa+arginine with octanol (4%), limonene (1.1-1.2%), lauroglycol (2%), water (5.2%), [all weight percent], propylene glycol and antioxidants can deliver, ex vivo, at least 6 mg/cm$^2$ carbidopa or levodopa through pig skin within 22 hours.

Example 3

Transdermal Delivery of Opipramol with Organic Hydrophilic Acids Ex Vivo

Figure 7A:
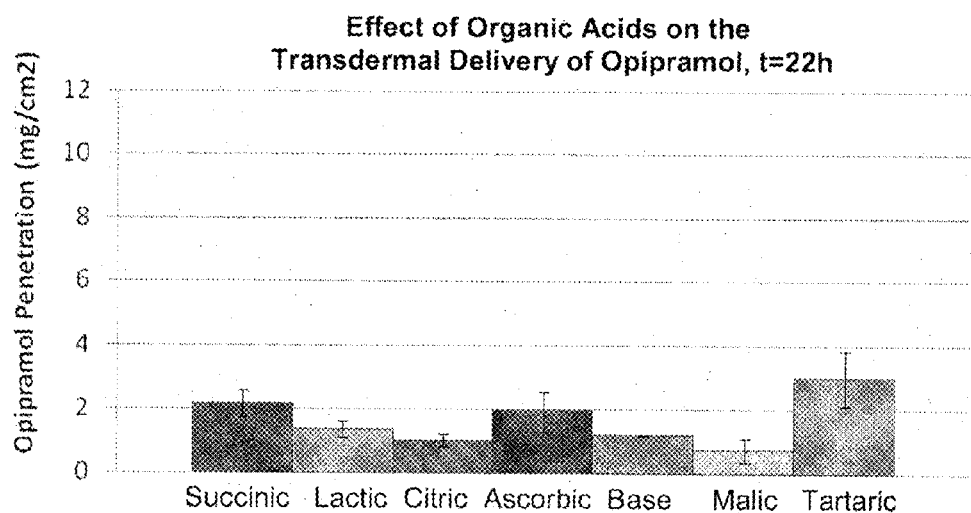
FIG. 7 depicts the effects organic acids on the transdermal delivery of opipramol through porcine skin ex vivo.
Figure 7B:
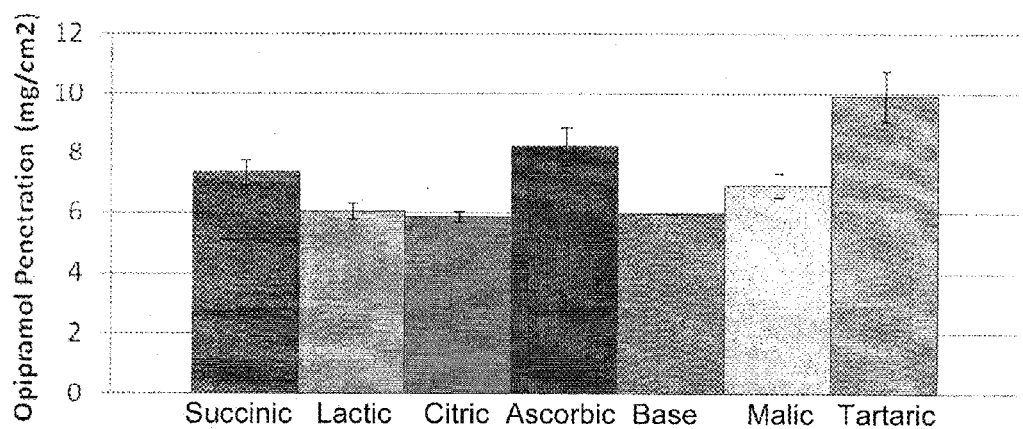

FIG. 7 depicts the effect of organic acids on the transdermal delivery of opipramol through full thickness pig skin. Formulations containing opipramol, various organic acids (succinic acid, citric acid, lactic acid, ascorbic acid, malic acid, or tartaric acid), octanol, lauroglycol, and/or Klucel® are prepared. Samples are collected from the receive cell at 22 and 46 hours after application of the formulations to the skin. The amount of opipramol compounds in the receiver cell fluid is determined using a spectrophotometer and/or UV-HPLC at 280 nm.

Results indicate that the addition of organic acids significantly increases the transdermal delivery of opipramol. Tartaric acid has the highest enhancing effect on opipramol delivery followed by ascorbic acid, succinic acid, and malic acid. Lactic acid and citric acid appear to have minimal effect on opipramol penetration through the skin.

Figure 8:
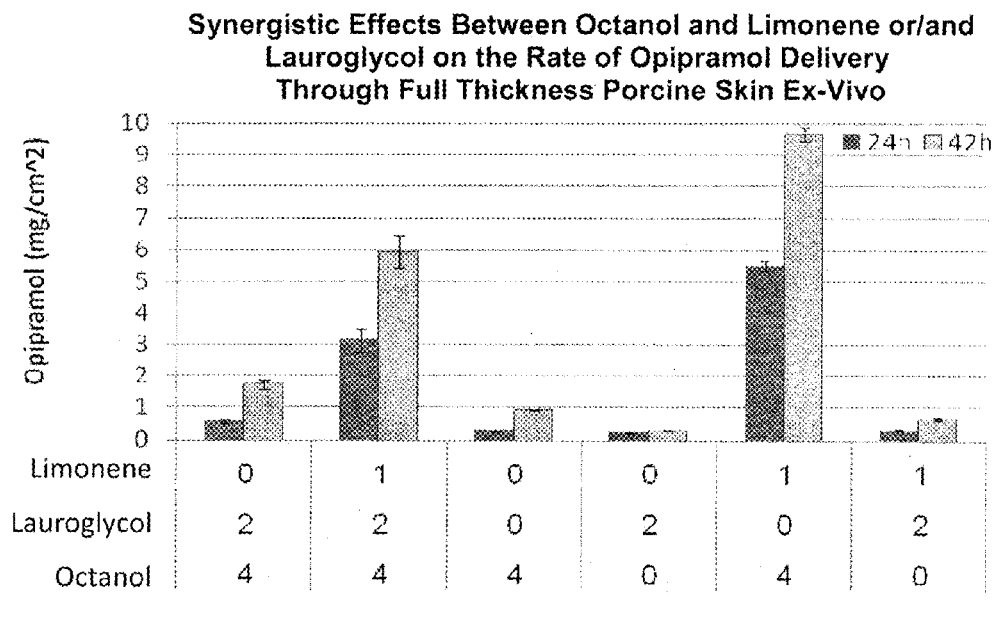
FIG. 8 depicts the effects of octanol, limonene and lauroglycol on the transdermal delivery of opipramol through porcine skin ex vivo.

FIG. 8 depicts the effects of octanol, limonene and/or lauroglycol on the transdermal delivery of opipramol (5% by weight) through full thickness pig skin. Results indicate that the combination of octanol and limonene provides an additive and/or synergistic effect on the delivery of opipramol through pig skin, ex vivo. The presence of lauroglycol in the formulation reduces the additive and/or synergistic effect of octanol and limonene on opipramol delivery, as shown in Table 3:

TABLE 3

Synergistic Effect between Octanol (O) and Limonene (L) or Lauroglycol (LG) and the Inhibitory Effect between Lauroglycol and Limonene

| | Experimental | | | | | | Calculated LG + | |
|---|---|---|---|---|---|---|---|---|
| | O F #3 | LG F #4 | LG/O F #1 | LG/L F #6 | L/O F #5 | L/LG/O F #2 | L + O F#1 + 6 | LG + O F#4 + 3 |
| 24 h | 0.3 | 0.2 | 0.6 | 0.3 | 5.5 | 3.1 | 0.9 | 0.5 |
| 42 h | 0.9 | 0.3 | 1.7 | 0.7 | 9.7 | 5.9 | 2.4 | 1.2 |

Figure 9:
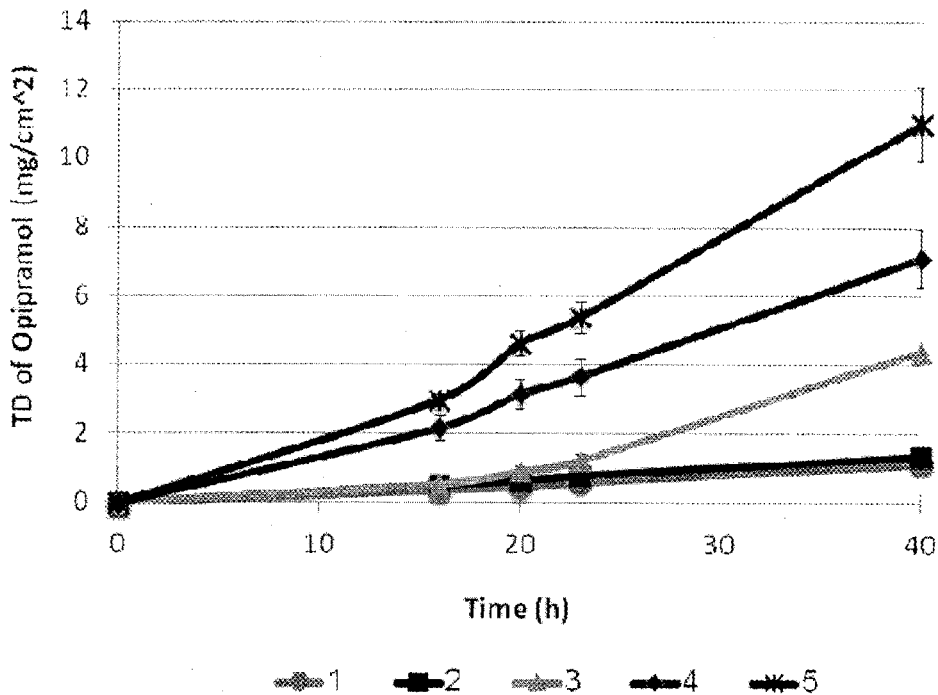
FIG. 9 depicts the effects of glutamic acid on the transdermal delivery of opipramol through porcine skin ex vivo.

FIG. 9 depicts the effect of glutamic acid on the transdermal delivery of opipramol through full thickness pig skin. Results indicate that glutamic acid significantly increases the opipramol penetration through the skin. In addition, the lag time of opipramol penetration through the skin is shortened in the presence of 5% water. However, the rate of penetration is reduced in the presence of 1% limonene.

Figure 10:
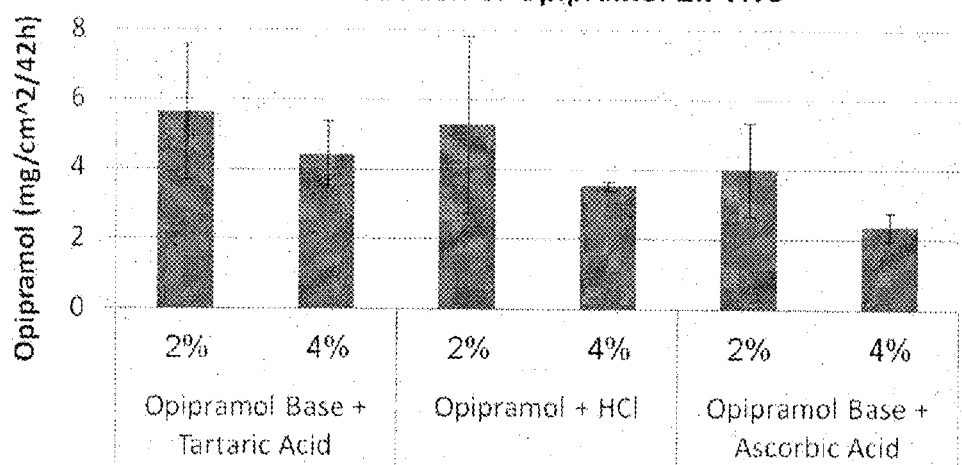
FIG. 10 depicts the effects of hydroxypropylcellulose on the transdermal delivery of opipramol through porcine skin ex vivo.

FIG. 10 depicts the effect of Klucel® hydroxypropyl cellulose on the transdermal delivery of opipramol. Increasing concentration of Klucel® within an opipramol formulation reduces the penetration of opipramol through the skin.

Figure 11:
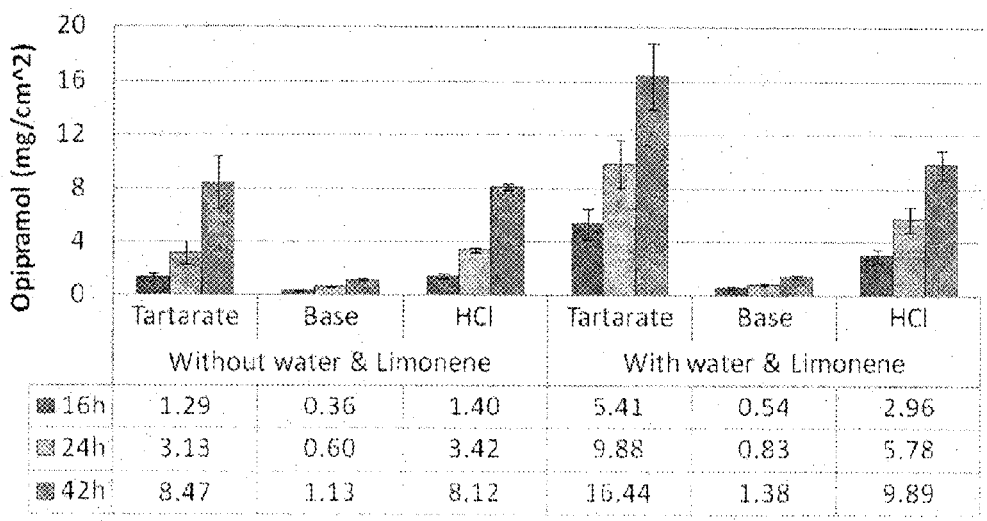
FIG. 11 depicts the effects of organic and non-organic acids on the transdermal delivery of opipramol through porcine skin ex vivo.

FIG. 11 compares the effect of tartaric acid and hydrochloric, non-organic acid on the transdermal delivery of opipramol through full thickness pig skin. Results indicate that tartaric acid significantly increases opipramol penetration through the skin as compared to opipramol base, and that tartaric acid was significantly superior to hydrochloric acid.

Figure 12:
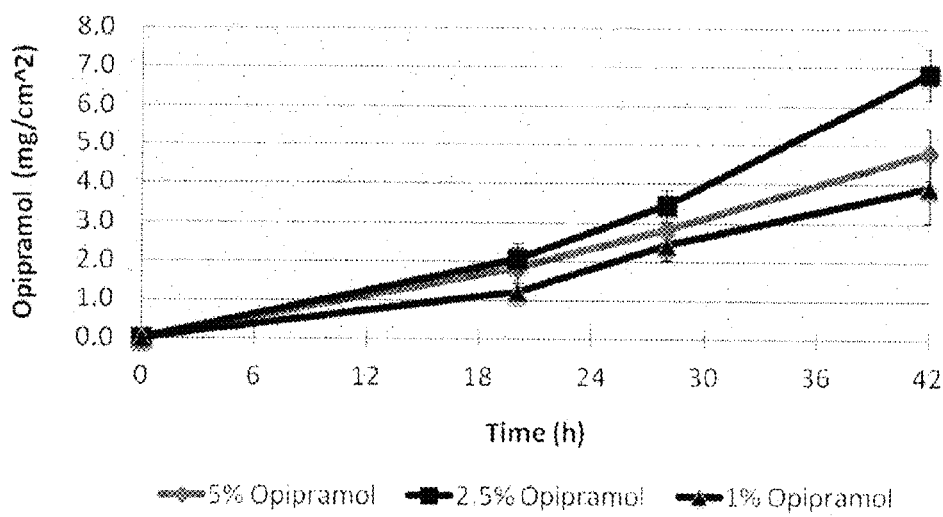
FIG. 12 depicts the dependence of transdermal delivery on the concentration of opipramol in a disclosed formulation.
Figure 13:
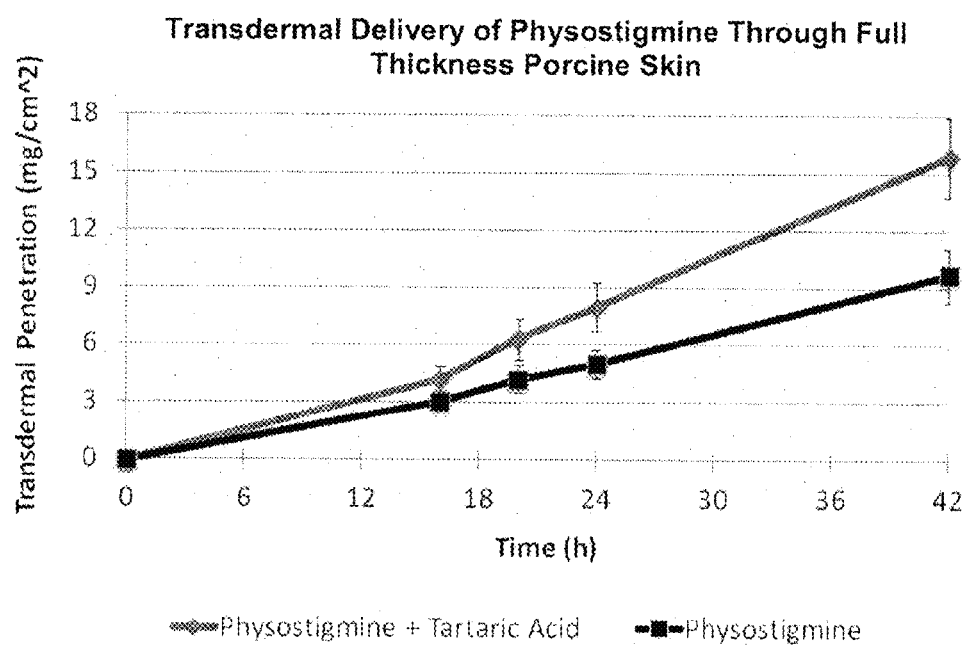
FIG. 13 depicts the transdermal delivery of physostigmine through porcine skin ex vivo.
Figure 14:
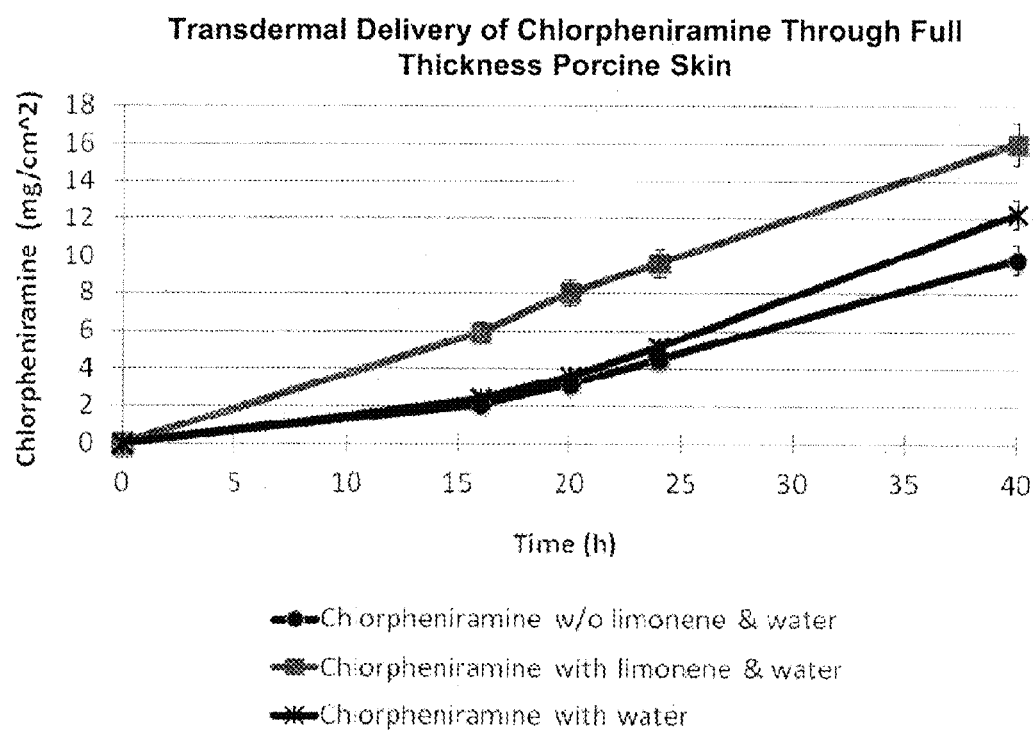
FIG. 14 depicts the transdermal delivery of chlorpheniramine through porcine skin ex vivo.
Figure 15:
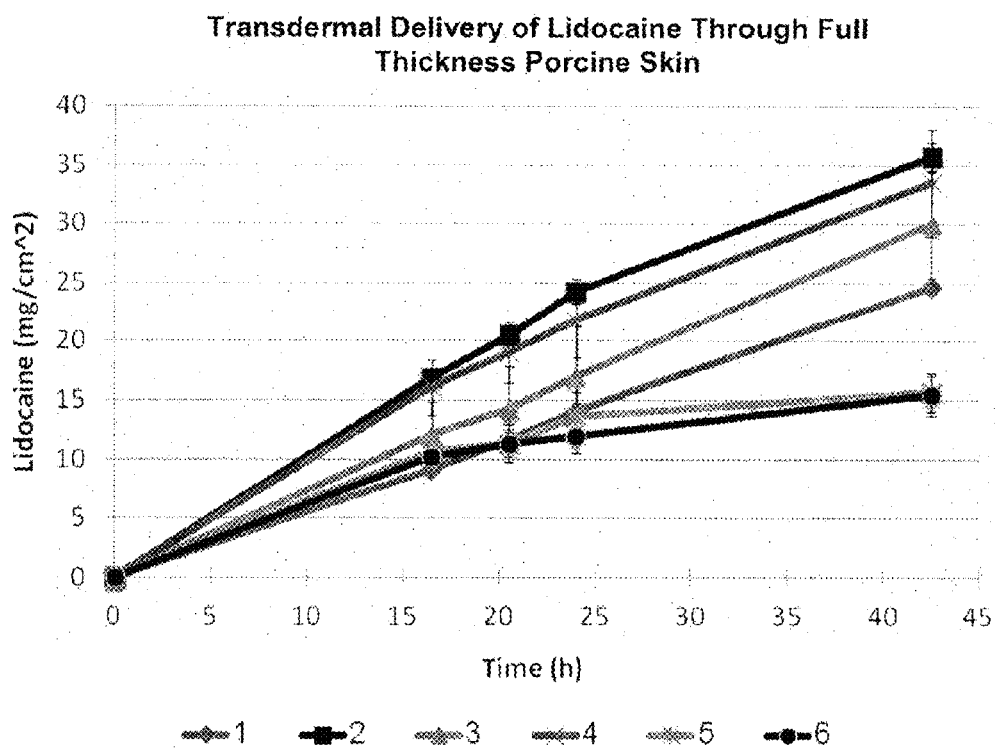
FIG. 15 depicts the transdermal delivery of lidocaine through porcine skin ex vivo.
Figure 16:
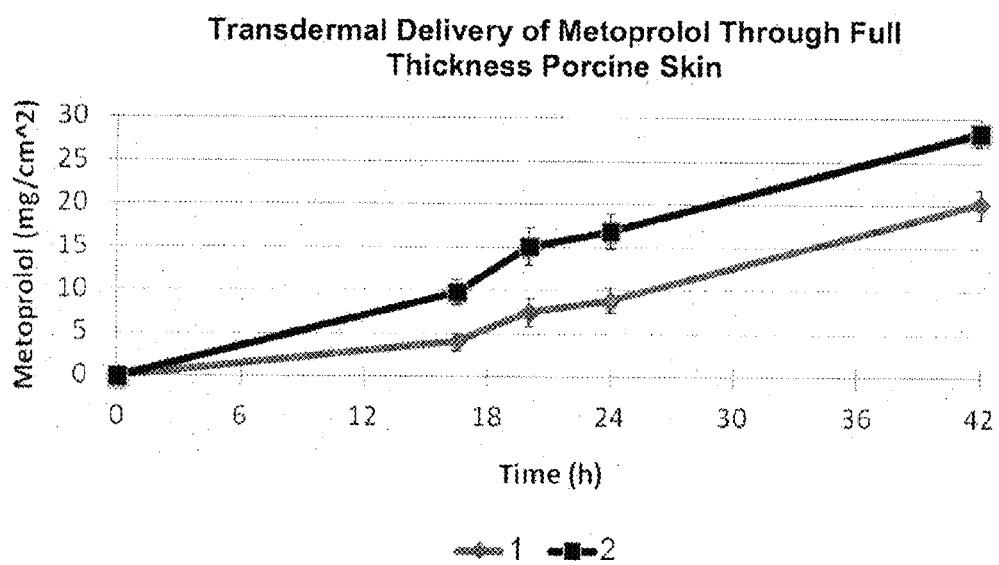
FIG. 16 depicts the transdermal delivery of metoprolol through porcine skin ex vivo.
Figure 17:
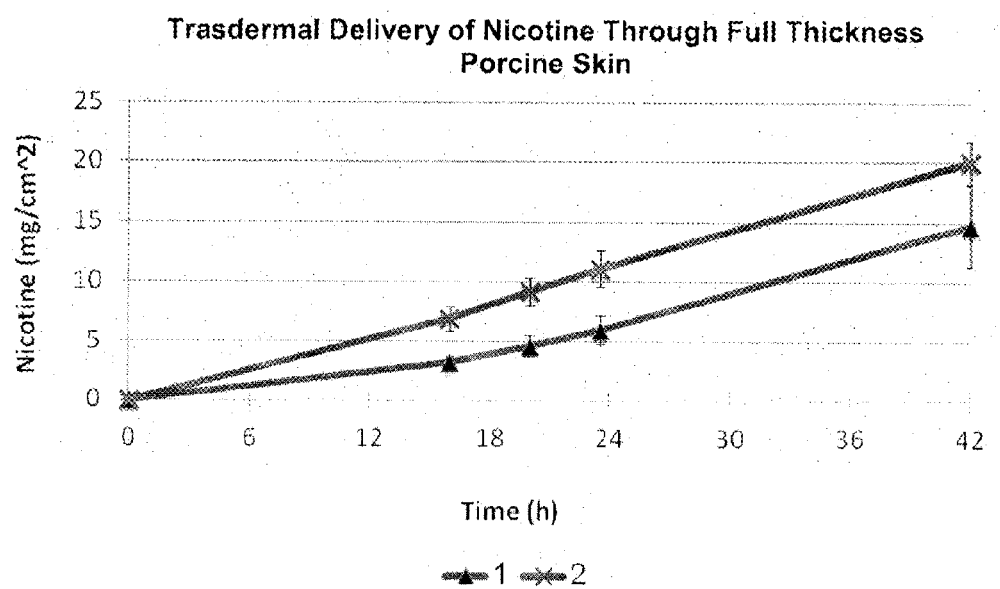
FIG. 17 depicts the transdermal delivery of nicotine through porcine skin ex vivo.
Figure 18:
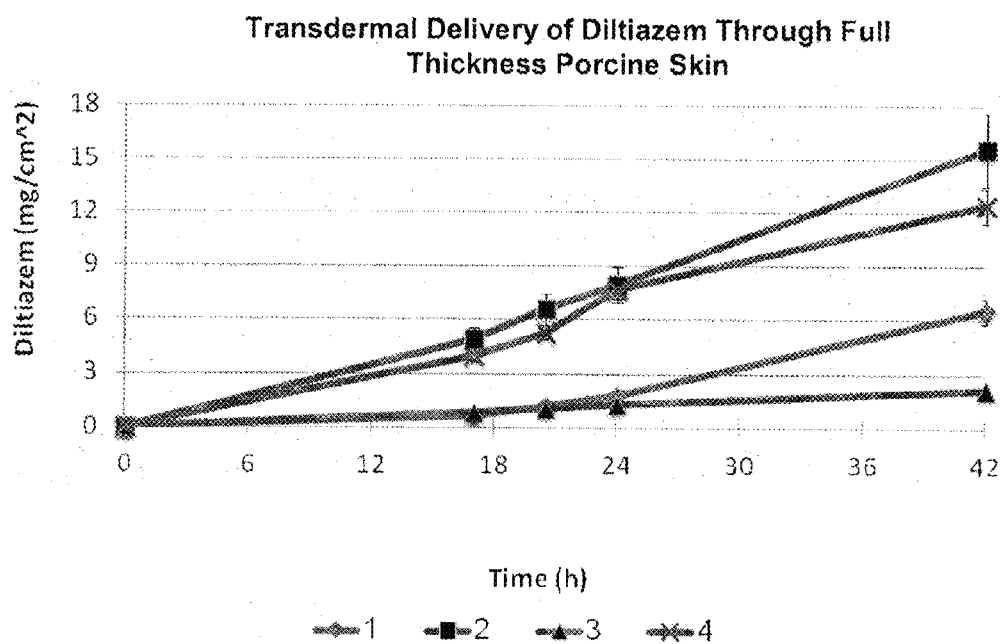
FIG. 18 depicts the transdermal delivery of diltiazem through porcine skin ex vivo.
Figure 19:
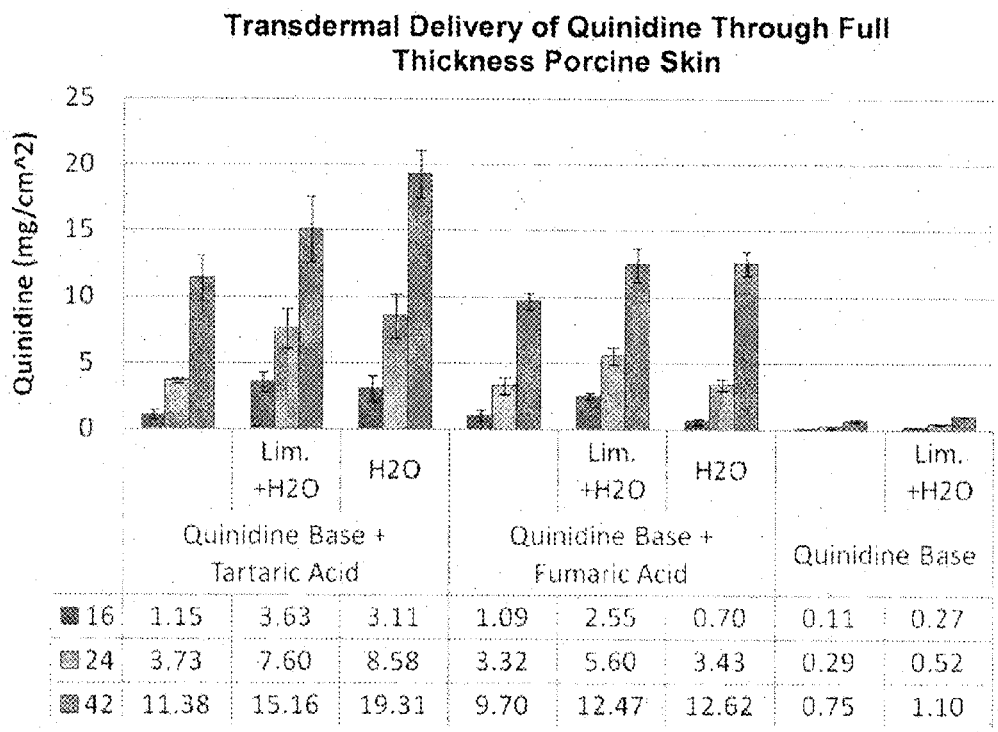
FIG. 19 depicts the transdermal delivery of quinidine through porcine skin ex vivo.
Figure 20:
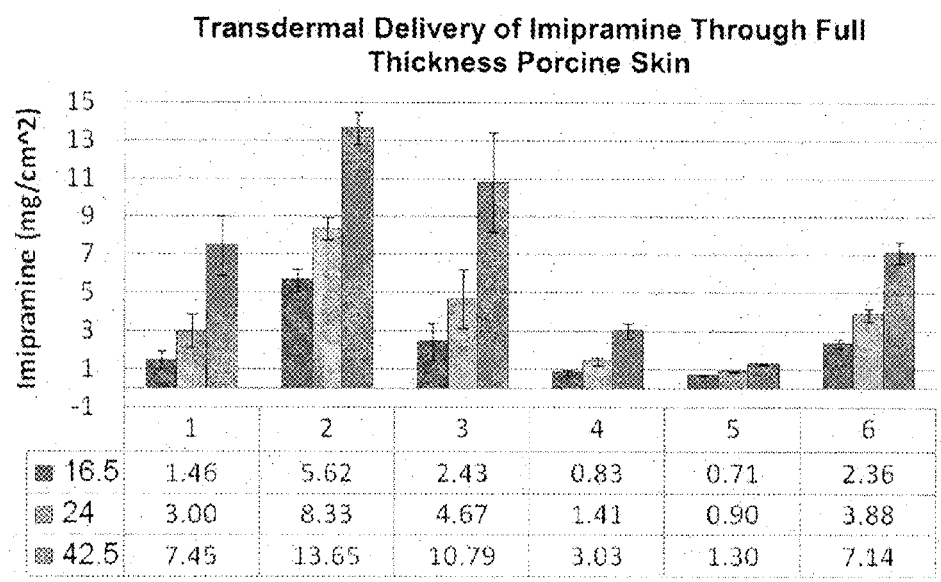
FIG. 20 depicts the transdermal delivery of imipramine through porcine skin ex vivo.
Figure 21:
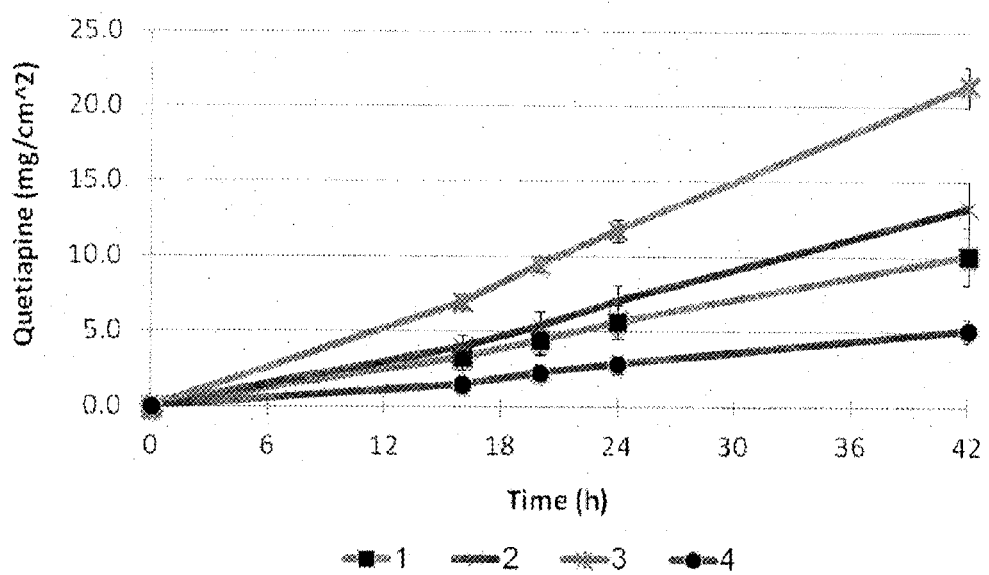
FIG. 21 depicts the transdermal delivery of quetiapine through porcine skin ex vivo.
Figure 22:
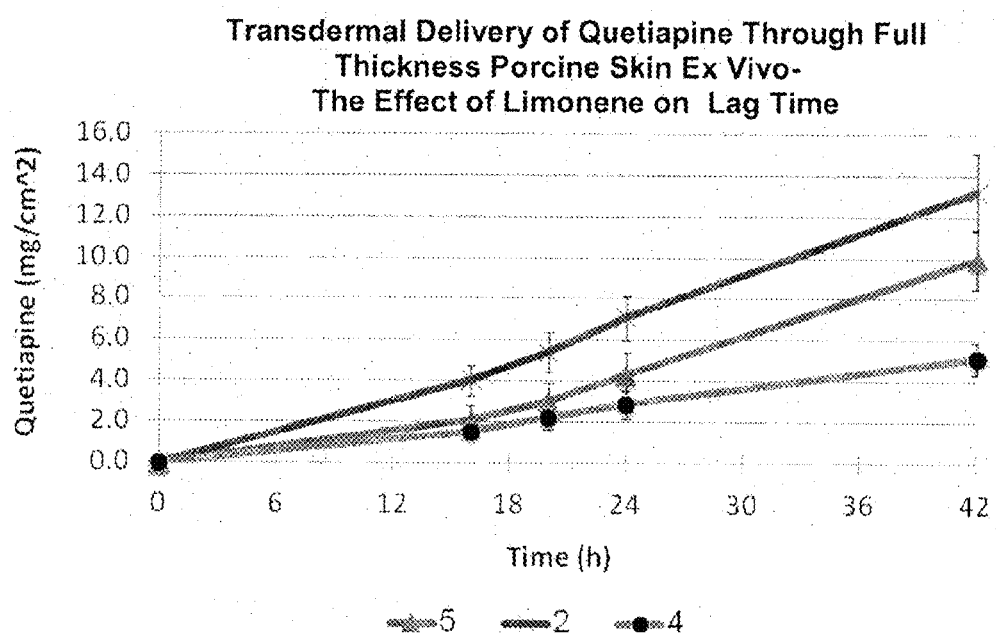
FIG. 22 depicts the effects of limonene on the lag time of the transdermal delivery of quetiapine through porcine skin ex vivo.
Figure 23:
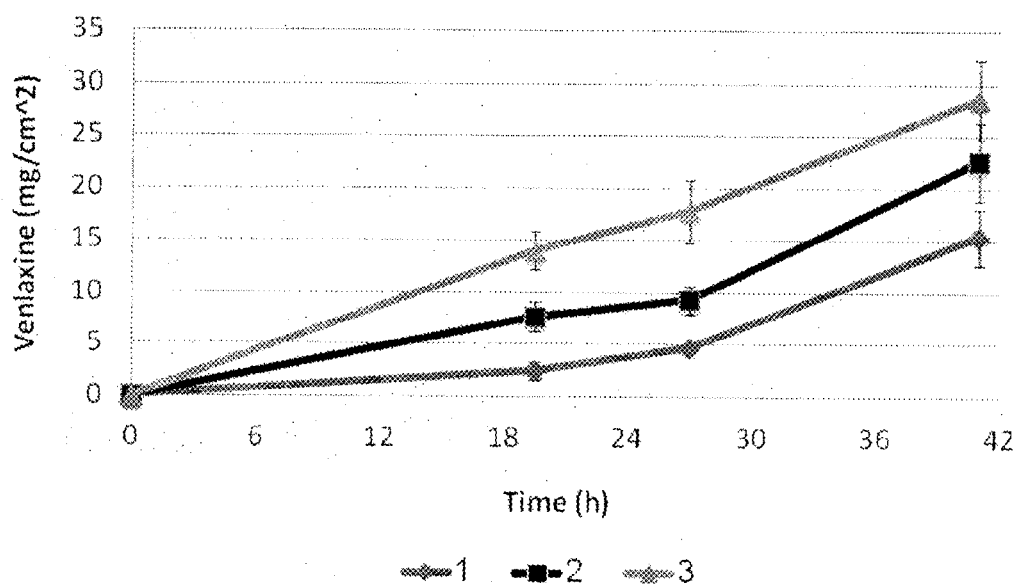
FIG. 23 depicts the effects of limonene on the lag time of the transdermal delivery of venlafaxine through porcine skin ex vivo.
Figure 24:
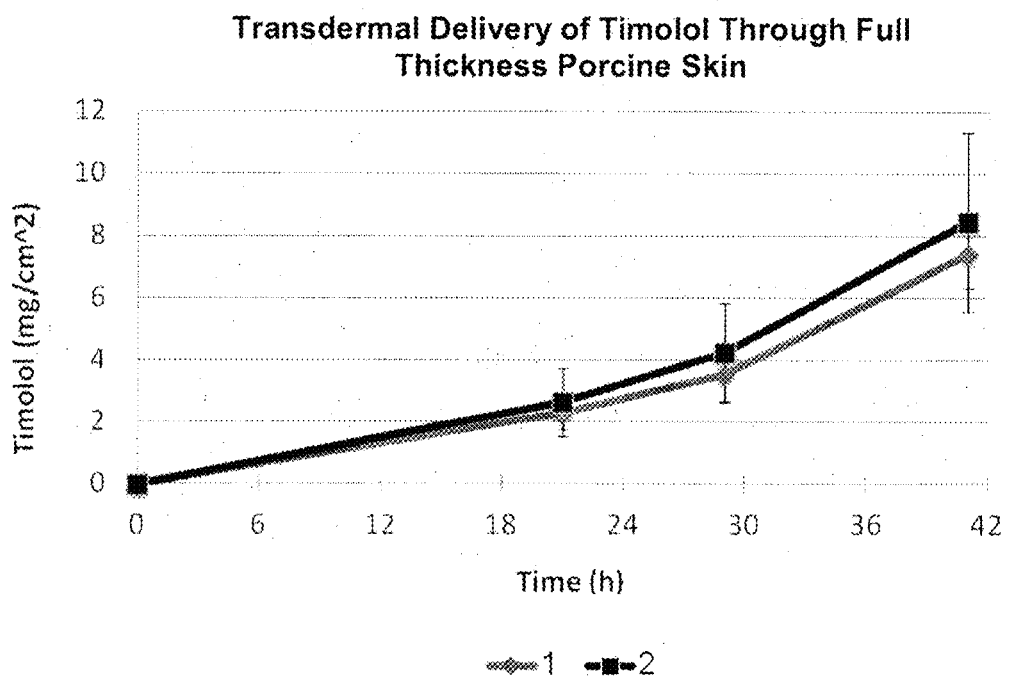
FIG. 24 depicts the transdermal delivery of timolol through porcine skin ex vivo.
Figure 25:
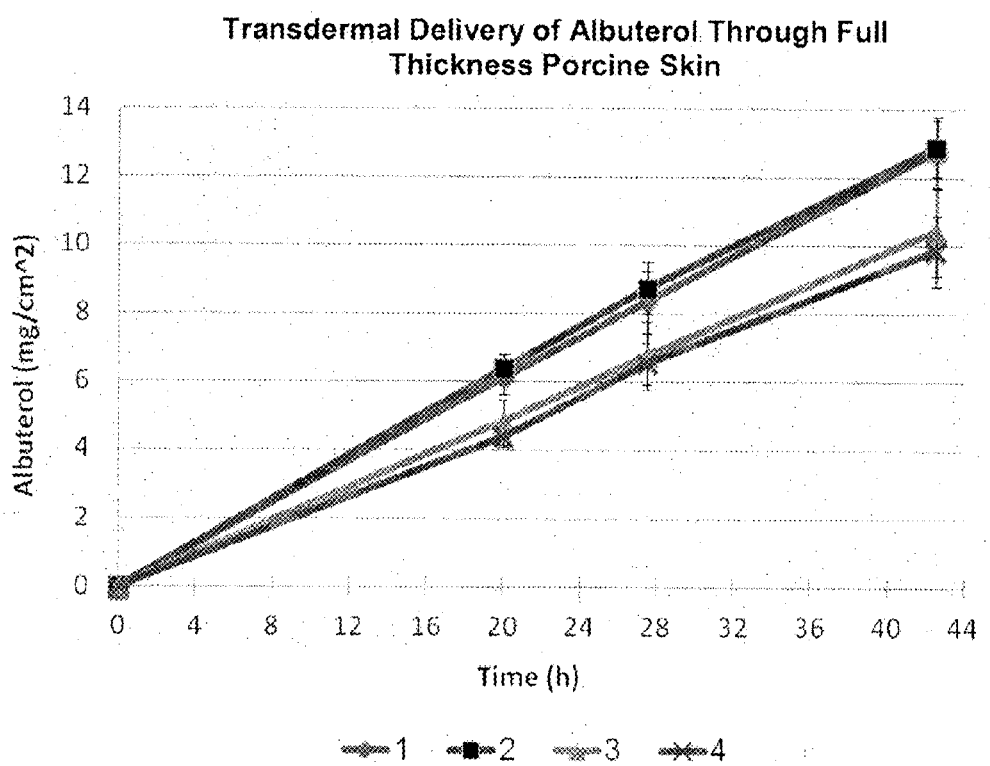
FIG. 25 depicts the transdermal delivery of albuterol through porcine skin ex viva.

FIG. 12 depicts the effect of octanol concentration in the formulation on the transdermal delivery of opipramol through full thickness pig skin. The figure shows that there is a positive correlation between the rate and total amount of opipramol transdermal delivery and opipramol concentration, i.e., formulation containing 2.5% (wt) opipramol concentration delivers more opipramol than the 1% formulation. The correlation is inversed when the concentration of opipramol in the formulation is 5%, i.e., the transdermal delivery of opipramol may be inhibited with higher concentration.

Example 4

Transdermal Delivery of Other Drug Compounds with an Amine Group Ex Vivo

FIGS. 13-26 depict the transdermal delivery of various drug compounds with an amine group through full thickness pig skin, ex vivo. The drug compounds are administered with organic acids. The concentrations of the tested compounds in the receiver cell are measured using a spectrophotometer as follows:

| Compound | Absorption (nm) | Molecular Weight | Transdermal Delivery (Figure #) |
|---|---|---|---|
| Opipramol | 254 | 364 | 8-12 |
| Physostigmine | 230 | 275 | 13 |
| Chlorphiniramine | 262 | 275 | 14 |
| Lidocanine | 263 | 234 | 15 |
| Metoprolol | 275 | 267 | 16 |
| Nicotine | 261 | 162 | 17 |
| Diltiazem | 237 | 415 | 18 |
| Quinidine | 331 | 324 | 19 |
| Imipramine | 250 | 280 | 20 |
| Quetiapine | 291 | 384 | 21-22 |
| Venlafaxine | 225 | 277 | 23 |
| Timolol | 293 | 316 | 24 |
| Albuterol | 276 | 239 | 25 |

The results indicate that formulations containing octanol, limonene, with or without lauroglycol significantly enhance the penetration of all amine compounds tested (with MW ranging between 162 and 415). Penetration was significantly increased in the presence of an organic acid as compared to the base form of the active compound. There was no correlation between the size of the compound and the extent of its penetration through the skin. For example, the penetration of chlorpheniramine (MW 275) was similar to that of diltiazem (MW 415).

Example 5

Figure 26:
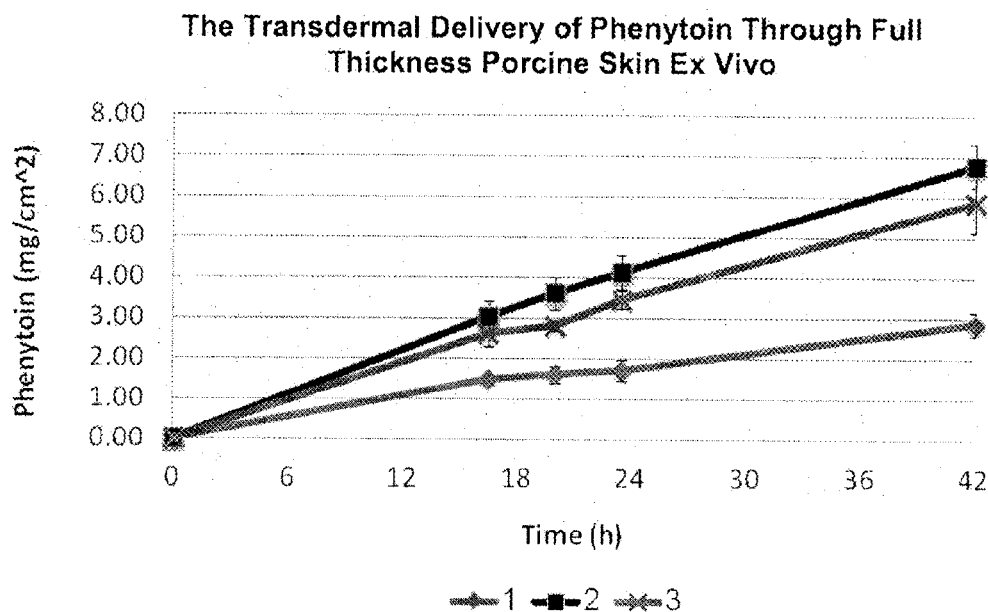
FIG. 26 depicts the transdermal delivery of phenytoin through porcine skin ex vivo.
Figure 27A:
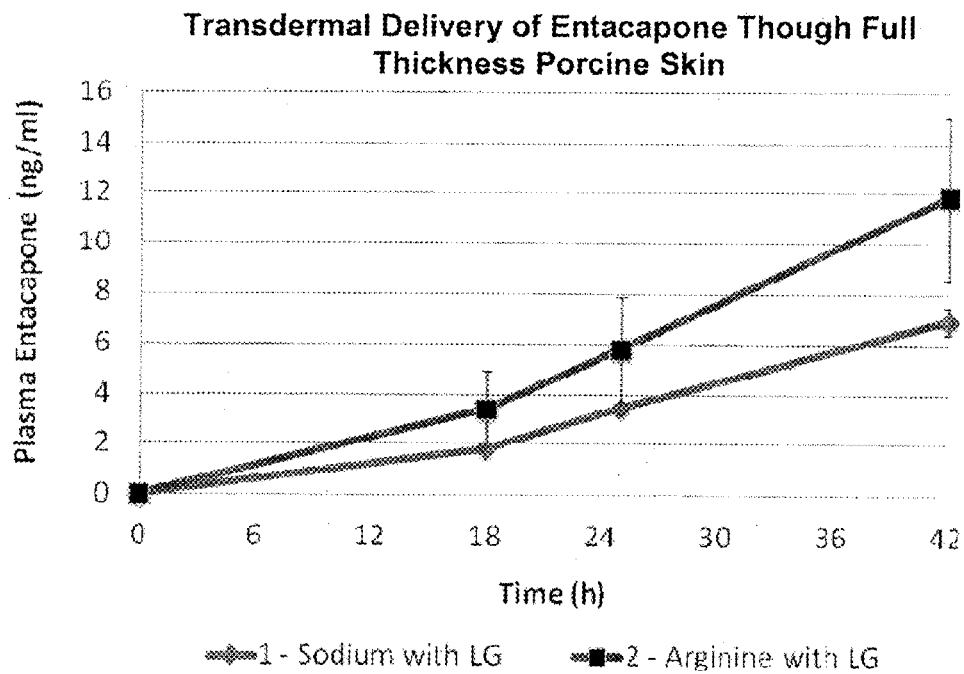
FIG. 27 depicts the transdermal delivery of entacapone through porcine skin ex vivo.
Figure 27B:
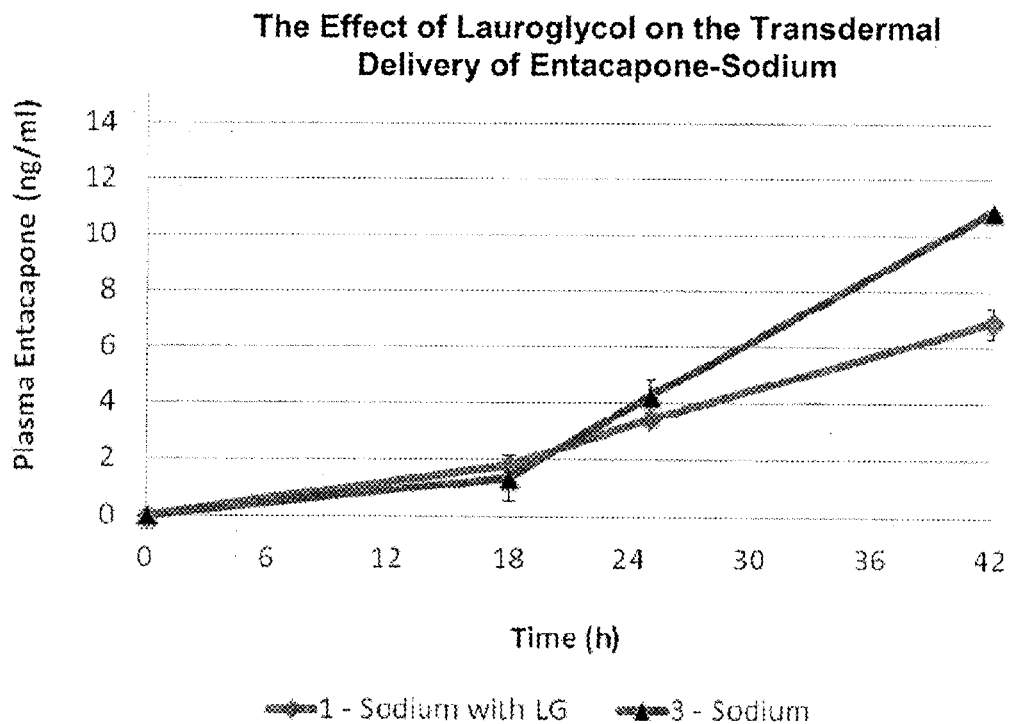
Figure 27C:
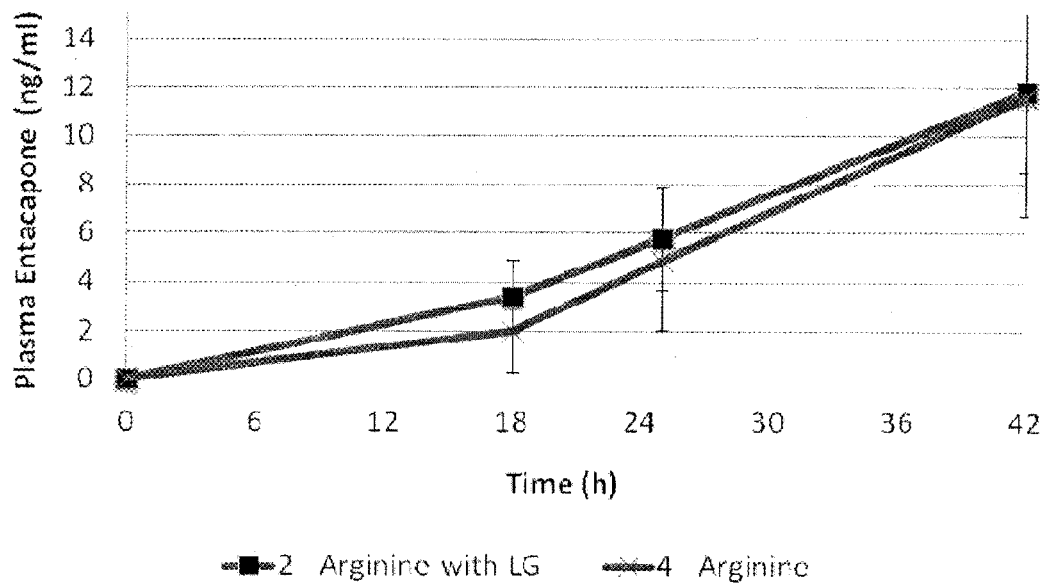
Figure 28:
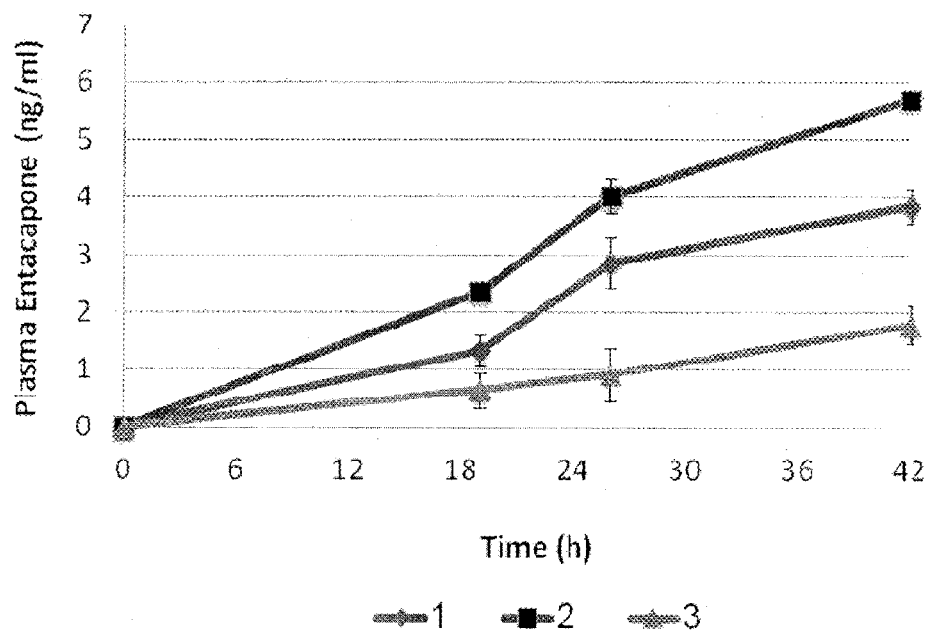
FIG. 28 depicts the effects of limonene on the lag time of the transdermal delivery of entacapone through porcine skin ex vivo.

Transdermal Delivery of Drug Compounds with a Negatively Charged Carbonyl Group Ex Vivo FIGS. 26-28 depict the transdermal delivery of various drug compounds, all having a negatively charged carbonyl group, through full thickness pig skin, ex vivo. The concentrations of the tested compounds in the receiver cell are measured using a spectrophotometer as follows:

| Compound | Absorption (nm) | Molecular Weight | TDD (Figure #) |
|---|---|---|---|
| Entacapone | 315 | 305 | 27, 28 |
| Phenytoin | 230 | 252 | 26 |

The results indicate that formulations containing octanol, limonene, with or without lauroglycol significantly enhance the penetration of the amine compounds tested.

Example 6

Transdermal Delivery of Carbidopa In Vivo

Figure 29A:
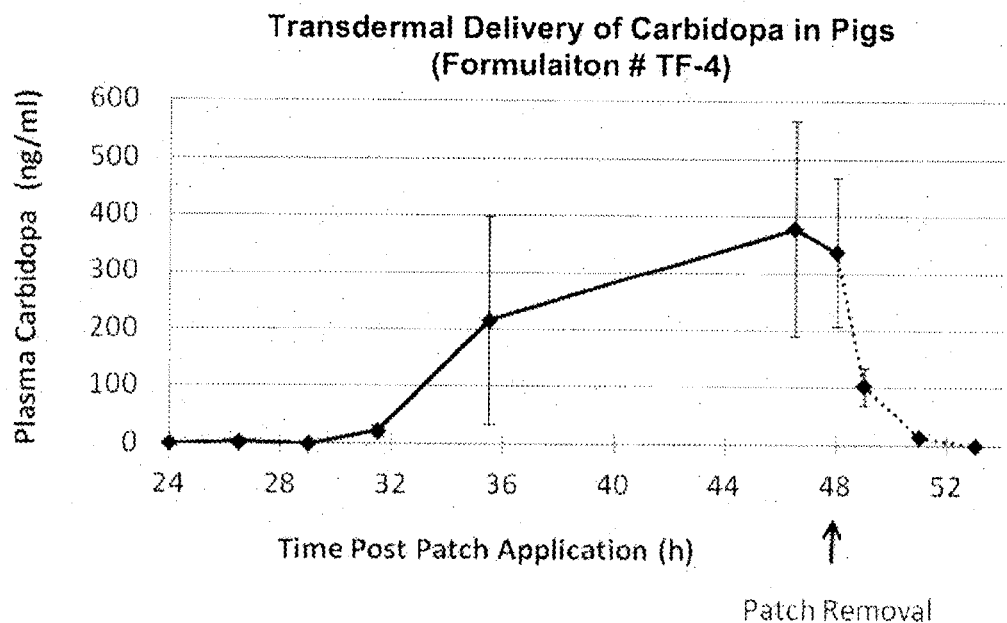
FIG. 29 shows the mean±SD of carbidopa concentrations (ng/ml) as detected in the plasma of female landrace×large white swine (15±2 kg) following the application of 2 transdermal carbidopa patches (28 $cm^2$/patch).
Figure 29B:
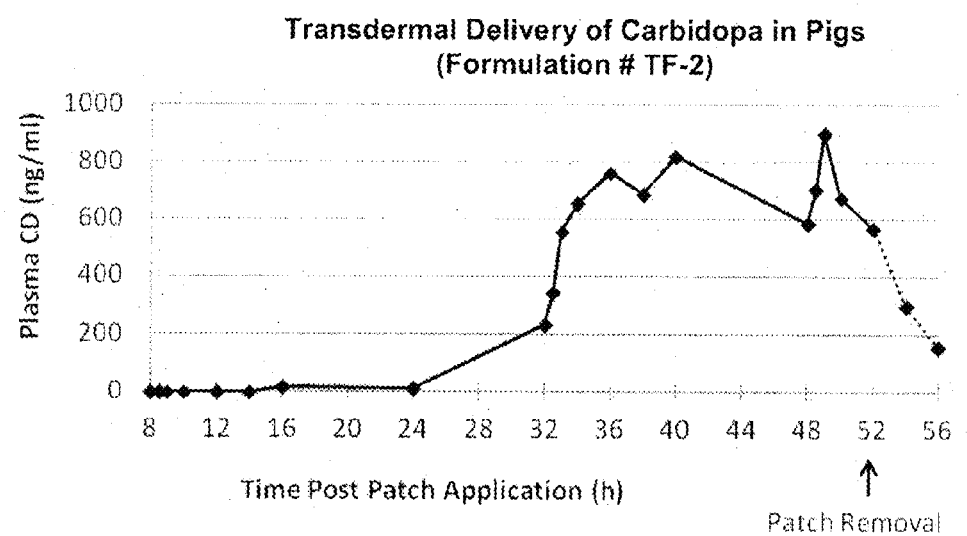

In this experiment, the purpose is to determine the transdermal delivery of carbidopa in pigs. Test Formulations, TF-2 and TF-4, each containing 14.5% carbidopa/arginine salt, octanol (4%), lauroglycol (2%), hydroxypropyl cellulose (4%), propylene glycol and water (5 and 10%, respectively) are applied to the back of pigs (12-15 kg). Blood samples are collected at pre-determined time points and plasma levels of carbidopa are analyzed by HPLC-ECD. FIG. 29 shows the mean±SD carbidopa plasma concentrations (ng/ml) following application of 2 transdermal patches (28 $cm^2$/patch).

Results show that both formulations are effective in the transdermal administration of carbidopa. Application of TF-2, which contains less water, results in a shorter lag time and higher steady state concentration of plasma carbidopa. TF-2 exhibits a 24 hour lag time and a steady state plasma concentration of carbidopa ranging between 600-900 ng/ml for a period of 20 hour, until patch removal. TF-4 exhibits a lag time of 30 hours and a steady state plasma concentrations of 300-400 ng/ml. Both formulations cause mild irritation after 48-52 hours of application.

Example 7

Transdermal Delivery of Metoprolol In Vivo

Figure 30:
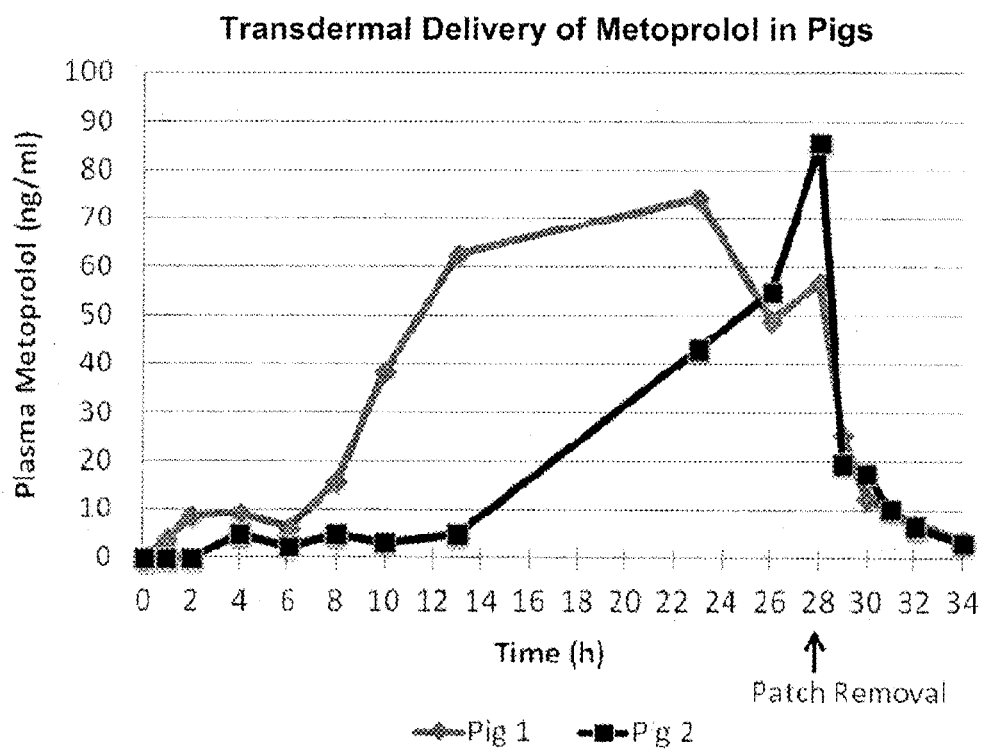
FIG. 30 shows the mean±SD of metoprolol concentrations (ng/ml) as detected in the plasma of female landrace×large white swine (15±2 kg) following the application of 2 transdermal metoprolol patches (28 $cm^2$/patch).

In this experiment, the purpose is to determine the transdermal delivery of metoprolol in pigs. Test Formulations containing 10% metoprolol and 2.8% tartaric acid, octanol (4%), limonene (1%), hydroxypropyl cellulose (3%), water (3%) and propylene glycol were applied to the back of pigs (12-15 kg). Blood samples were collected at pre-determined time points and plasma levels of metoprolol were analyzed by HPLC-UV. FIG. 30 shows the metoprolol plasma concentrations (ng/ml) following application of 2 transdermal patches (28 $cm^2$/patch).

Results show that the formulation was effective in the transdermal administration of metoprolol. Application of the metoprolol formulation results in a lag time of 5-13 hours and a steady state concentration of plasma metoprolol. The formulation caused mild and transient irritation after 24 hours of application.

Equivalents

Those skilled in the art will recognize, or be able to ascertain using no more than routine experimentation, many equivalents to the specific embodiments of the invention described herein. Such equivalents are intended to be encompassed by the following claims.

Incorporation By Reference

The entire contents of all patents, published patent applications, websites, and other references cited herein are hereby expressly incorporated herein in their entireties by reference.

The invention claimed is:

1. A pharmaceutically acceptable transdermal composition comprising octanol, a terpene, an organic acid, and an active agent or pharmaceutically acceptable salts thereof, wherein the transdermal composition, when transdermally administered to a patient, delivers more than twice the amount of the active agent to said patient over 20 hours as compared to a formulation that does not include octanol; a formulation that does not include hydrocarbon terpene; or a formulation that does not include an organic acid.

2. The pharmaceutically acceptable transdermal composition of claim 1, wherein the organic acid is selected from the group consisting of ascorbic acid, tartaric acid, malic acid, succinic acid, fumaric acid, citric acid, lactic acid, glutamic acid, and aspartic acid.

3. The pharmaceutically acceptable transdermal composition of claim 2, further comprising a basic amino acid selected from the group consisting of arginine, lysine and histidine.

4. The pharmaceutically acceptable transdermal composition of claim 1, wherein the active agent is selected from the group consisting of carbidopa, levodopa, and pharmaceutically acceptable salts thereof.

5. The pharmaceutically acceptable transdermal composition of claim 1, wherein the active agent is selected from the group consisting of opipramol, physostigmine, chlorpheniramine, lidocaine, metoprolol, nicotine, salbutamol, timolol, diltiazem, quinidine, imipramine, quetiapine, venlafaxine, and pharmaceutically acceptable salts thereof.

6. The pharmaceutically acceptable transdermal composition of claim 1, wherein (i) the composition has about 1 to about 10 weight percent active agent; and/or (ii) the composition has about 1 to about 5 weight percent octanol.

7. The pharmaceutically acceptable transdermal composition of claim 1, wherein the composition has about 0.25 to about 5 weight percent terpene.

8. The pharmaceutically acceptable transdermal composition of claim 1, wherein the terpene is d-limonene.

9. The pharmaceutically acceptable transdermal composition of claim 1, further comprising a fatty acid ester, wherein the composition has about 0.1 to about 5.0 weight percent fatty acid ester.

10. A pharmaceutically acceptable transdermal composition comprising octanol, limonene, organic acid, and opipramol or pharmaceutically acceptable salts thereof, wherein the transdermal composition, when transdermally administered to a patient, delivers more than twice the amount of opipramol to said patient over 20 hours as compared to a formulation that does not include octanol; a formulation that does not include limonene; or a formulation that does not include an organic acid.

11. The pharmaceutically acceptable transdermal composition of claim 10, wherein the organic acid is selected from the group consisting of ascorbic acid, tartaric acid, malic acid, succinic acid, fumaric acid, citric acid, lactic acid, glutamic acid, and aspartic acid.

12. The pharmaceutically acceptable transdermal composition of claim 10, further comprising a basic amino acid selected from arginine, lysine and histidine.

13. The pharmaceutically acceptable transdermal composition of claim 10, wherein (i) the composition has about 0.5 to about 7.5 weight percent octanol; and/or (ii) the composition has about 0.25 to about 5 weight percent limonene.

14. The pharmaceutically acceptable transdermal composition of claim 10, further comprising lauroglycol.

15. The pharmaceutically acceptable transdermal composition of claim 14, wherein the weight ratio of octanol to lauroglycol is about 3:1 to about 1.5:1.

16. The pharmaceutically acceptable transdermal composition of claim 12, wherein the basic amino acid is arginine.

17. The pharmaceutically acceptable transdermal composition of claim 9, further comprising wherein the fatty acid ester is lauroglycol.

18. The pharmaceutically acceptable transdermal composition of claim 17, wherein the weight ratio of octanol to lauroglycol is about 3:1 to about 1.5:1.

* * * * *